(12) United States Patent
Su et al.

(10) Patent No.: US 10,568,663 B2
(45) Date of Patent: Feb. 25, 2020

(54) SPINAL SURGICAL INSTRUMENT, METHOD OF GUIDING THEREOF AND SYSTEM FOR BONE STABILIZATION

(71) Applicant: WILTROM CO., LTD., Zhubei (TW)

(72) Inventors: Yi-Chun Su, Zhubei (TW); Sherwin Hua, Zhubei (TW); Hsiang-Ming Huang, Zhubei (TW); Huang-Chien Liang, Zhubei (TW); Chieh-Feng Lu, Zhubei (TW); Huang-Chi Chen, Zhubei (TW)

(73) Assignee: Wiltrom Co., Ltd., Zhubei, Hsinchu County (TW)

( * ) Notice: Subject to any disclaimer, the term of this patent is extended or adjusted under 35 U.S.C. 154(b) by 101 days.

(21) Appl. No.: 15/702,086

(22) Filed: Sep. 12, 2017

(65) Prior Publication Data
US 2018/0070987 A1     Mar. 15, 2018

(30) Foreign Application Priority Data

Sep. 12, 2016  (TW) .............................. 105129654 A
Jun. 20, 2017  (TW) .............................. 106120638 A

(51) Int. Cl.
| A61B 17/70 | (2006.01) |
| A61B 90/92 | (2016.01) |
| A61B 17/88 | (2006.01) |
| A61B 90/00 | (2016.01) |

(52) U.S. Cl.
CPC ........ *A61B 17/7001* (2013.01); *A61B 17/708* (2013.01); *A61B 17/7037* (2013.01); *A61B 17/7083* (2013.01); *A61B 17/7091* (2013.01); *A61B 17/8875* (2013.01); *A61B 17/8888* (2013.01); *A61B 17/8897* (2013.01); *A61B 90/92* (2016.02); *A61B 17/7032* (2013.01); *A61B 2090/031* (2016.02); *A61B 2090/037* (2016.02)

(58) Field of Classification Search
CPC ........................................ A61B 17/7074–7091
See application file for complete search history.

(56) References Cited

U.S. PATENT DOCUMENTS

| 8,236,032 B2 * | 8/2012 | Ramsay ............. | A61B 17/7032 606/279 |
| 9,486,256 B1 * | 11/2016 | Lish ................... | A61B 17/7086 |
| 10,034,690 B2 * | 7/2018 | Heflin ................ | A61B 17/7037 |
| 2002/0169450 A1 * | 11/2002 | Lange ................ | A61B 17/7037 606/250 |

(Continued)

*Primary Examiner* — Jacqueline T Johanas
*Assistant Examiner* — Michelle C Eckman
(74) *Attorney, Agent, or Firm* — Muncy, Geissler, Olds & Lowe, P.C.

(57) ABSTRACT

The present invention discloses a spinal surgical instrument and a method of guiding thereof. The spinal surgical instrument is operated with a precedent device. The precedent device includes at least one guiding unit. The spinal surgical instrument includes an operating element, an extending element, a handling element and a guide element. One end of the extending element connects to the operating element. The other end of the extending element connects to the handling element. The guide element is disposed on the extending element and includes at least one guide hole. The operating element is guided to the precedent device by the passing of the guide hole along the guiding unit.

15 Claims, 20 Drawing Sheets

(56) References Cited

U.S. PATENT DOCUMENTS

| | | | |
|---|---|---|---|
| 2006/0247658 A1* | 11/2006 | Pond, Jr. | A61B 17/7082 606/104 |
| 2007/0073294 A1* | 3/2007 | Chin | A61B 17/7037 606/86 A |
| 2008/0195155 A1* | 8/2008 | Hoffman | A61B 17/7091 606/278 |
| 2009/0270916 A1* | 10/2009 | Ramsay | A61B 17/1735 606/246 |
| 2010/0114179 A1* | 5/2010 | Moore | A61B 17/7032 606/308 |
| 2010/0168796 A1* | 7/2010 | Eliasen | A61B 17/7035 606/264 |
| 2010/0249844 A1* | 9/2010 | Durrani | A61B 17/025 606/259 |
| 2010/0292739 A1* | 11/2010 | Schwab | A61B 17/7032 606/305 |
| 2011/0319938 A1* | 12/2011 | Piza Vallespir | A61B 17/7076 606/264 |
| 2012/0209332 A1* | 8/2012 | Janowski | A61B 17/7038 606/278 |
| 2013/0079827 A1* | 3/2013 | Neary | A61B 17/7077 606/264 |
| 2013/0096635 A1* | 4/2013 | Wall | A61B 17/7085 606/305 |
| 2013/0103096 A1* | 4/2013 | Miller | A61B 17/7032 606/305 |
| 2014/0275793 A1* | 9/2014 | Song | A61B 17/0218 600/204 |
| 2015/0164561 A1* | 6/2015 | Simpson | A61B 17/7002 606/264 |
| 2016/0106480 A1* | 4/2016 | Zhou | A61B 17/7002 606/86 A |
| 2018/0070987 A1* | 3/2018 | Su | A61B 17/7001 |
| 2019/0069930 A1* | 3/2019 | Su | A61B 17/7032 |

* cited by examiner

SPINAL SURGICAL INSTRUMENT, METHOD OF GUIDING THEREOF AND SYSTEM FOR BONE STABILIZATION

BACKGROUND OF THE INVENTION

1. Field of the Invention

The present invention relates generally to a surgical instrument, a method of guiding thereof and a system for bone stabilization, particularly to a spinal surgical instrument and a method of guiding thereof.

2. Description of the Related Art

The vertebral column is a major component of the central nervous system of the human body. Spinal disorders, especially in the lumbar region, often have a considerable impact on patients, causing pain, numbness, weakness, incontinence, dysuria, dyschezia, or other symptoms. The above symptoms are caused by a translocation between vertebral bodies oppressing the nerve or spinal cord. Due to different mechanisms, spinal disorders are clinically diagnosed as disc herniation, spondylolisthesis, spinal stenosis or degenerative scoliosis. When symptoms are severe, the discomfort of patients usually cannot be relieved by correction, and spinal surgery is required to reposition the vertebrae. An important key to treatment success is the effective fixation of the repositioned vertebral body to prevent subsequent displacement.

The pedicle screw fixation system, a spinal implant device applied in vertebral fusion surgery, is the most stable and prevalent treatment for vertebral reposition and fixation in traditional intervertebral disc resection, cervical degeneration and scoliosis correction. To assemble a pedicle screw fixation system on target vertebrae, a surgeon must use several kinds of surgical instruments in surgery. The most difficult aspect of such surgery is locating implanted devices such as pedicle screws before approaching them with different surgical instruments in every move of the entire procedure. Furthermore, the approach of the surgical instruments must be very accurate. The effectiveness and efficiency of this procedure will tremendously influence surgery outcomes and the recovery time of patients.

The pedicle screw fixation system includes a plurality of pedicle screws. In the case of a multi-axial pedicle screw, each pedicle includes three major parts: a screw shaft, a tulip and an inner cap (also known as a retainer ring). In addition, pedicle screw is combined with a locking screw (also known as a nut). A common surgical procedure of the pedicle screw fixation system involves a first step of inserting pedicle screws in pairs into the pedicles of each vertebra on the spinous processes on both sides of the vertebra. After that, rods are adjusted to match the normal vertebral curve, and then the locking screw is fixed into the tulip together with the rod by a pre-lock wrench and an anti-torque wrench. Once the rods are locked in the tulips, two adjacent vertebral bodies are correspondingly repositioned or stabilized. If necessary, surgeons will adjust the angles of the pedicle screws with a pedicle screw adjuster during surgery.

When manipulating the abovementioned surgical instruments, a surgeon has to individually insert them from the outside of a patient's body into the incision and then move them to the positions of the pedicle screws. However, because of muscle and ligament tissues around the incision, the surgeon cannot easily locate the implanted pedicle screws during surgery. To locate the screws, surgeons have to separate or distract those tissues from the vertebrae constantly, and sometimes, even removal of a part of a vertebra is necessary. This approach is accompanied by an increase in blood loss, slower recovery due to anatomical destruction, severe postoperative pain, higher postoperative infection rate and other adverse effects. Post-operative recovery in such cases can greatly extend the length of hospital stay and increase medical costs.

Besides the pedicle screw fixation system, other spine surgeries also require the use of numerous different surgical instruments. For example, non-fusion fixation is used for the treatment of spinal stenosis, mild spondylolisthesis, or adjacent segmental disc disease. Compared with the pedicle screw fixation system, non-fusion fixation surgery allows the vertebrae to have a larger active range and prevents early degradation of adjacent vertebrae. However, locating the implanted devices and then approaching those devices with instruments accurately are necessary steps in the injection of bone grafts or bone cement, or in expansion of the implanted cage in non-fusion fixation surgery, in order to ensure the effectiveness and low damage of the surgery.

In recent years, the clinical importance of minimally invasive spinal surgery has been increasing, and it has gained favor with surgeons and patients. Minimally invasive spinal surgery can be performed with the newly developed cortical bone trajectory (CBT) screw technique and cortical screw, which is considered a new treatment rather than traditional surgery.

The aim of minimally invasive spinal surgery is to provide a shorter recovery term for patients. However, in such surgery, surgeons have much less operative space than in traditional surgery to manipulate surgical instruments. In addition, since the muscles and connective tissues of patients block surgeons' operative field, the visibility of patients' internal physical structures is limited. Thus, it is more difficult to locate the implanted screw in minimally invasive surgery than in traditional invasive surgery. The abovementioned issues increase the difficulty of the engagement of a rod or a surgical instrument with a screw. Increased difficulty and pressure on a surgeon manipulating the instrument may prolong the operation time, resulting in a burden on the patient. In many cases, the surgeon must rely on touch to ensure positioning. These difficulties indirectly discourage surgeons from performing minimally invasive surgery.

Accordingly, for conventional or minimally invasive spinal surgery, a crucial issue is whether the surgeon can repeatedly locate an implanted screw or an expander (referred to herein as precedent devices) and then move instruments to the position stably. Furthermore, the inconvenience of locating the screws and guiding surgical instruments to the screws in minimally invasive surgery can be reduced so as to greatly increase of the incidence of minimally invasive surgery in hospitals.

SUMMARY OF THE INVENTION

In view of the above problems, it is a major objective of the present invention to provide a spinal surgical instrument and a method of guiding it to approach a precedent device. The spinal surgical instrument includes an operating element and a guide element. The guide element has guide holes such that it can be used with a precedent device having a guiding unit. By the passing of the guide hole of the spinal surgical instrument along the guiding unit of the precedent device, the spinal surgical instrument can be smoothly guided to approach the precedent device. Therefore, the difficulty of locating a precedent device accurately is reduced, and the difficulty of moving the surgical instrument to the position stably is addressed.

To achieve the above objective, the present invention provides a spinal surgical instrument operated with a precedent device. The precedent device includes at least one guiding unit. The spinal surgical instrument includes an operating element, an extending element, a handling element, and a guide element. One end of the extending element connects to the operating element. The opposite end of the extending element connects to the handling element. The guide element is disposed on the extending element and includes at least one guide hole. The spinal surgical instrument is guided to approach the precedent device by the passing of the guide hole along the guiding unit.

According to an embodiment of the present invention, the guide element is set in the extending element or integrally formed with the extending element.

According to an embodiment of the present invention, the distance between the guide element and the operating element is shorter than the distance between the guide element and the handling element.

According to an embodiment of the present invention, the distance between the guide element and the operating element is about 0 mm.

According to an embodiment of the present invention, the width of the guide element close to an end of the handling element is greater than the width of the guide element close to an end of the operating element.

According to an embodiment of the present invention, the guide element has a groove located at the periphery of the guide hole, by which the guide hole communicates with the outer space.

According to an embodiment of the present invention, the guide element has a blocker located between the groove and the guide hole.

According to an embodiment of the present invention, the guide element has at least two guide holes, which are located on the side opposite the extending element along a center line described by the extension of the extending element.

According to an embodiment of the present invention, the operating element has at least one longitudinal groove. The spinal surgical instrument includes an adjustable element and a rod element. The rod element is disposed through the handling element, the extending element and part of the operating element, and can be movably connected with the adjustable element. The opposite end of the rod element is accommodated in the operating element. When the adjustable element is moved, it will drive the rod element to move within the operating element to enable the operating element to expand.

According to an embodiment of the present invention, the operating element has an accommodating space, and the rod element has an expansion head accommodated in the accommodating space. In addition, the outer wall slope of the expansion head is greater than the inner wall slope of the accommodating space.

According to an embodiment of the present invention, the distance between the guide element and the operating element is about 0 mm. The guide element has a bottom edge and a side wall. The bottom edge is connected to the operating element, and the side wall is partially connected to the extending element.

According to embodiment of the present invention, the guide hole runs through the side wall.

According to an embodiment of the present invention, the guide element has at least two guide holes, one of which is adjacent to the extending element, and the other of which is adjacent to the operating element. The guide holes communicate with each other.

According to an embodiment of the present invention, the spinal surgical instrument is a pre-lock wrench, a pedicle screw adjuster, a rod holder, a bone cement or repair material injector, an anti-torque wrench, or a breaker.

To achieve the above objective, it is another objective of the present invention to provide a method of enabling a spinal surgical instrument to approach a precedent device. The precedent device includes at least on guiding unit. The spinal surgical instrument includes an operating element, an extending element, handling element, and a guide element. An end of the extending element connects to the operating element, and the opposite end of the extending element connects to the handling element. The guide element is disposed at the extending element and has at least one guide hole. The method includes the following steps: passing the guide hole along the guiding unit, and guiding the spinal surgical instrument to the precedent device.

According to an embodiment of the present invention, the method further includes the following step: assembling the guiding unit with the precedent device.

According to an embodiment of the present invention, the method further includes the following step: moving the guiding unit toward the precedent device by moving the guide hole along the guiding unit, such that the operating element is assembled with the precedent device.

As described above, the spinal surgical instrument and the method of guiding thereof according to the present invention are used in conjunction with a precedent device having a guiding unit. The spinal surgical instrument includes an operating element, an extending element, a handling element and a guide element. The two ends of the extending element connect to the operating element and the handling element, respectively. In addition, the guide element is disposed on the extending element, and the guide element has a guide hole. By aligning the guide hole with the guiding unit and then making the guiding unit pass through the guide hole, the surgeon can move the spinal surgical instrument along the guiding unit in a predetermined direction to efficiently and effectively approach the precedent device for subsequent moves. Therefore, the design of the present invention addresses the problems of a limited operative space and narrow operative field encountered by surgeons during surgery. In addition, the use of the present invention can reduce the influence of the adverse effects of retraction or detachment of tissue, improve the success rate of surgery, reduce the operation time and shorten the period of postoperative recovery.

In addition, the spinal surgical instrument of the present invention can be any instrument used for placing a pedicle screw fixation system or cortical bone trajectory (CBT) screw technique. Thus, even if surgeons have to change instruments during the procedure, each of the instruments can be guided to move along a predetermined path following the guiding unit by the guiding unit passing through the guide hole. In this way, the surgeon can ensure that the spinal surgical instruments move toward or away from the screw following the original path to reduce the expansion of an incision.

Especially for minimally invasive surgery, the guiding unit of a precedent device can protrude from the surgical incision on the back of a patient, so the surgeon can clearly recognize the location of the implanted or precedent device. It is also useful for surgeons to identify or align the approach direction of surgical instruments with the guiding unit during the subsequent moves.

DETAILED DESCRIPTION OF THE PREFERRED EMBODIMENT

In order to make the structure and characteristics as well as the effectiveness of the present invention to be further understood and recognized, the detailed description of the present invention is provided as follows along with embodiments and accompanying figures.

The spinal surgical instrument disclosed in the present invention is operated with a precedent device for treatment, correction, improvement, or relief of spinal disorders or to prevent the deterioration thereof. Particularly, in one embodiment, the surgical treatment is achieved by a pedicle screw fixation system, wherein the precedent devices are pedicle screws. In the pedicle screw fixation system, the precedent devices are paired in multiple pairs, such as six or eight pairs. The spinal surgical instrument, which can be a pre-lock wrench, pedicle screw adjuster, rod holder, bone cement or repair material injector, anti-torque wrench, or breaker, is any tool or instrument used in the operative procedure of the pedicle screw fixation system. The pedicle screw fixation system is used in the following as an example to illustrate the present invention. However, the present invention is not limited to the pedicle screw fixation system. Other surgical treatments such as the cortical bone trajectory screw technique, fusion surgery using intervertebral or intravertebral cages or expanders, or a variety of treatments wherein a specific device is implanted in or anchored to a vertebra and then the subsequent operation of instruments in conjunction with the device can be the applications of the present invention.

Figure 1A:
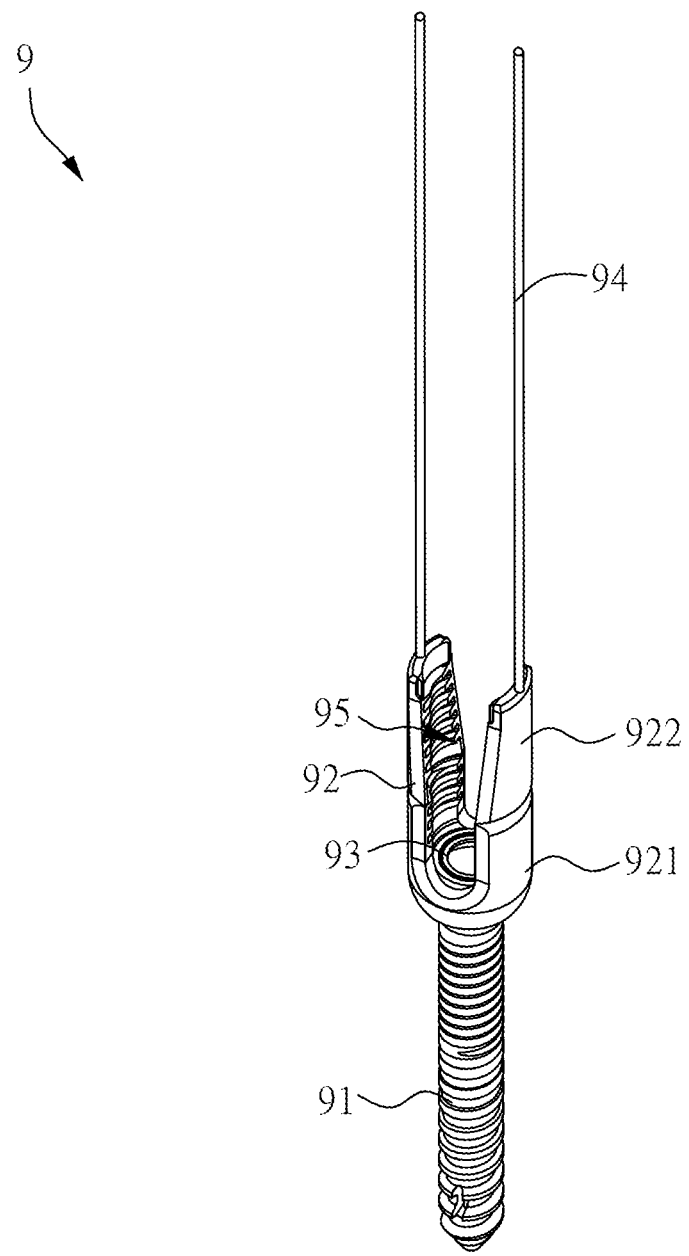
FIG. 1A is a schematic diagram of a precedent device.
Figure 1B:
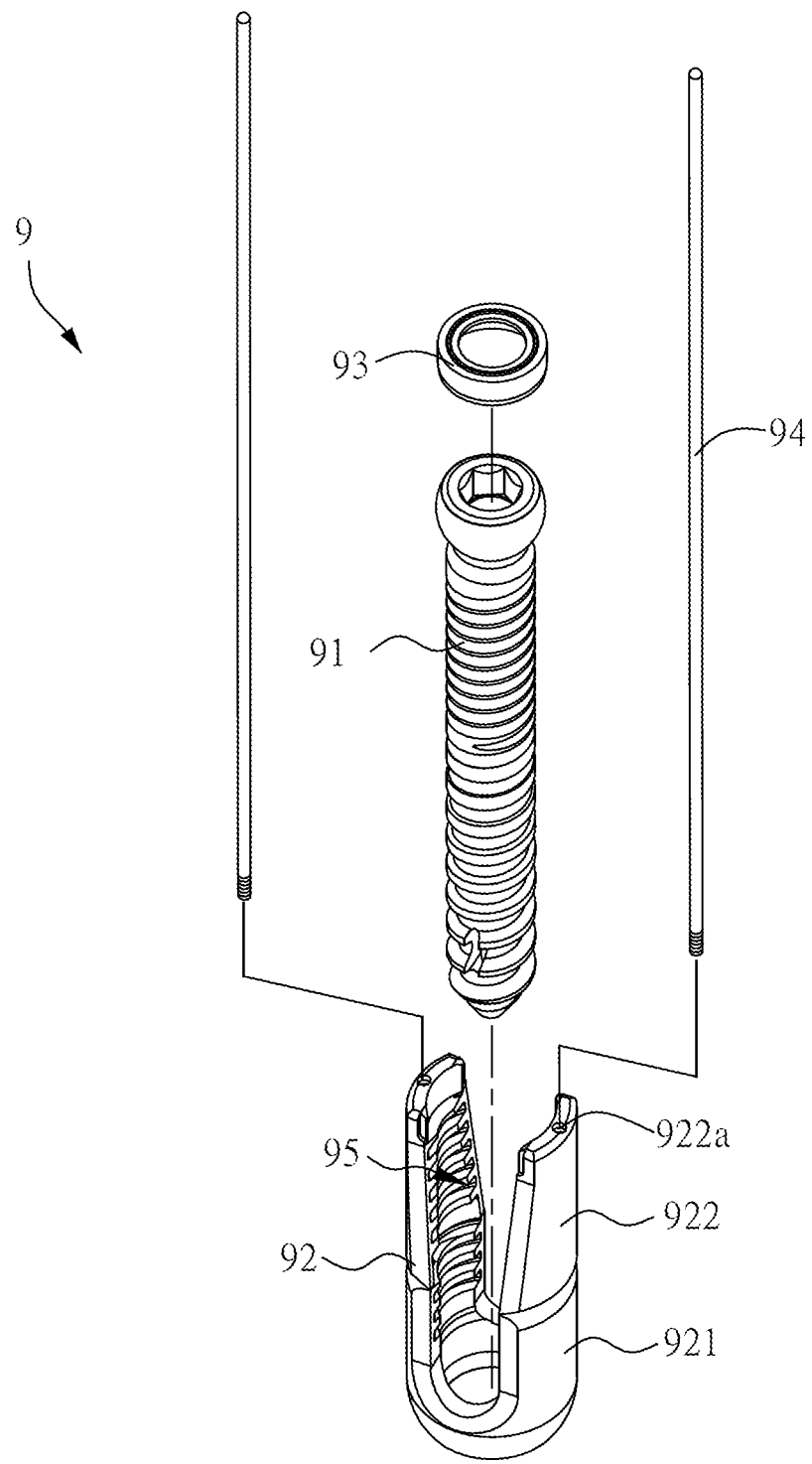
FIG. 1B is an exploded view of the precedent device shown in FIG. 1A.
Figure 1C:
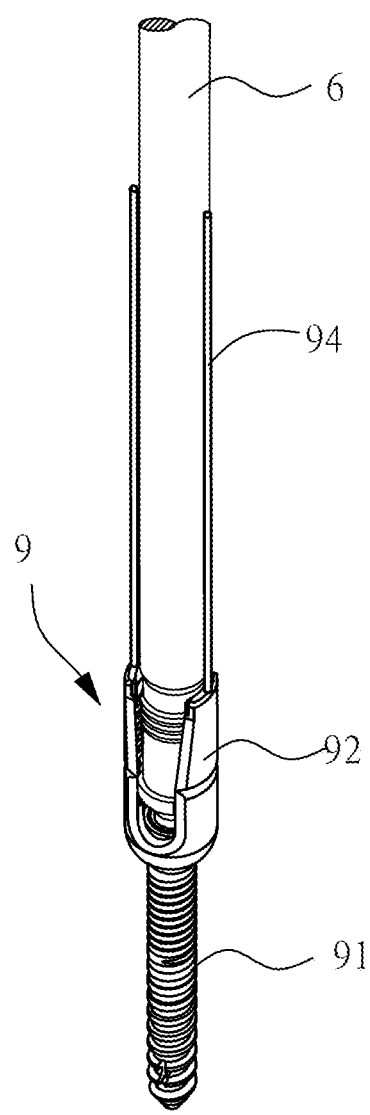
FIG. 1C is a schematic diagram for assembling the precedent device shown in FIG. 1A to prepare for implantation.
Figure 1D:
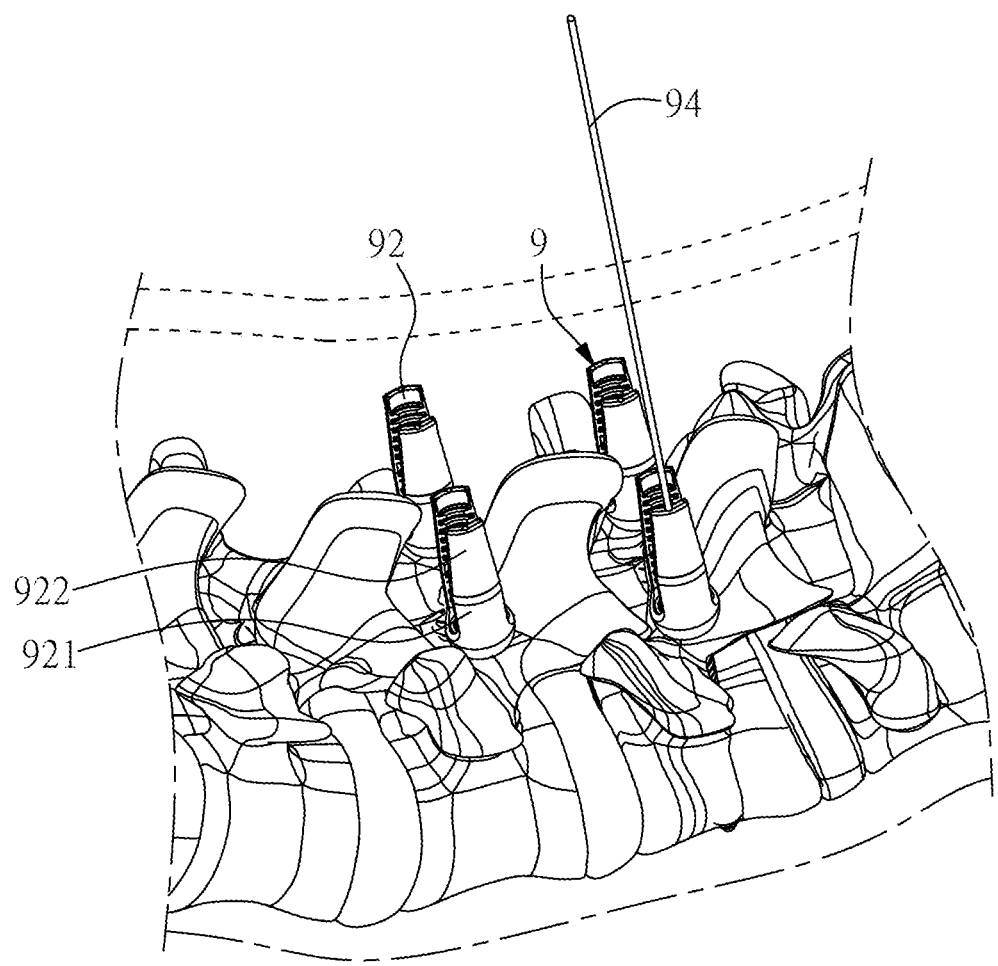
FIG. 1D is a schematic diagram showing the precedent device shown in FIG. 1A implanted in a vertebral body.
Figure 1E:
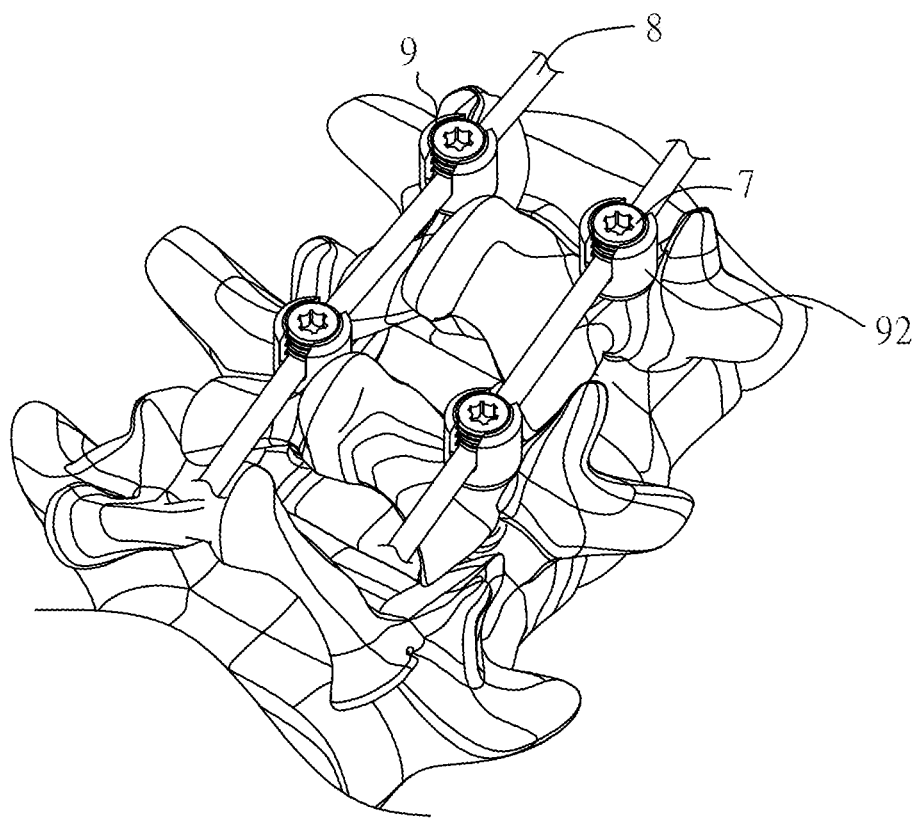
FIG. 1E is a schematic diagram showing the use of a pedicle screw fixation system containing the precedent device shown in FIG. 1A for treatment of vertebral lesions.

FIG. 1A is a schematic diagram of a precedent device of one embodiment of the present invention. FIG. 1B is an exploded view of the precedent device shown in FIG. 1A. FIG. 1C is a schematic diagram of assembly of the precedent device shown in FIG. 1A for implantation. FIG. 1D is a schematic diagram showing the precedent device shown in FIG. 1A being implanted into a vertebra. FIG. 1E is a schematic diagram showing the use of a pedicle screw fixation system containing the precedent device shown in FIG. 1A for treatment of spinal disorders. Please refer to FIG. 1A to FIG. 1E. The precedent device 9 in the present embodiment is a pedicle screw. The reference to the pedicle screw as a precedent device in the present embodiment is based on the need to implant a pedicle screw in the vertebra before the application of a series of spinal surgical instruments and accessories on the implanted pedicle screw for completing the pedicle screw fixation system during the surgery.

In the present embodiment, the precedent device 9 includes a screw shaft 91, a receiver 92, an inner cap 93 and at least one guiding unit 94. The receiver 92 is usually U-shaped and thus can be called a U-shaped head, U-head, tulip or tulip head. The middle recess of the receiver 92 defines an accommodating space 95 used for accommodating a rod 8 and a screw nut 7 fastening the rod 8. The screw shaft 91 and the receiver 92 may be integrally formed or may be connected as a spherical joint as shown in the figure. In terms of commercial products, the former is called a single-axis screw or monoaxial screw, and the latter is called a multi-axial or universal screw or polyaxial screw.

A thread on the screw shaft 91 can be customized depending on the location of the implantation. One screw has a shaft having the same pitches evenly distributed around the cylinder of the screw's body and is called a pedicle screw. Another screw has a shaft having shorter pitches in the upper portion and longer pitches in the lower portion and is called a cortical screw. However, the present invention is not limited to any type of the screws mentioned herein.

The receiver 92 can be further divided into an engaging seat 921 and a removable part 922. As shown in FIG. 1B, during assembly of the precedent device 9, the screw shaft 91 is first passed through the accommodating space 95. Because the diameter of the spherical head of the screw shaft 91 is greater than the inner diameter of the perforation below the accommodating space 95, the spherical head of the screw shaft 91 is stuck in the lower perforation. After an inner cap 93 is placed on the spherical head of the screw shaft 91, the screw shall 91 and the inner cap 93 are pressed into the lower perforations together for fixation to the engaging seat 921 by a jig. The top surfaces of the removable parts 922 have openings 922a corresponding to the number of the guiding units 94. In the present embodiment, each of the top surfaces of the removable parts 922 has an opening 922a. Preferably, the opening 922a is located in the middle of the top surface of a removable part 922 and has an internal thread for connection with the guiding unit 94 in a screwed manner. The guiding unit 94 has a long rod structure, which also known as a guiding shaft or a guiding pole. The length of the guiding unit 94 is about 7 to 20 cm, preferably about 10 to 15 cm. The diameter of the guiding unit 94 is or less than about 0.2 cm and preferably about 0.1 to 0.2 cm. The guiding unit 94 can be made of various biocompatible and rigid materials such as titanium. In addition, the precedent device 9 in the present invention can have one guiding unit 94 but preferably two guiding units 94 disposed at the top surfaces of the removable parts 922 on both sides of the receiver 92. The guiding units 94 also have other functions that conventional K-pins or K-wires cannot provide. For example, one is to assist surgeons to determine the orientation of the receiver 92, and another is to facilitate smooth engagement of the operating element 11 and the receiver 92.

Spinal disorders often occur in patients' lumbar region, especially in the lumbar L4, L5, so the pedicle screw fixation system is often implanted in the lumbar L4, L5. Before that, the surgeon has to create a screw channel by using an instrument such as an awl to create an entry point on the lumbar vertebrae and then boring through a pedicle to the cancellous bone of the vertebra. Then the surgeon can choose whether to expand or tap the screw channel to prepare for screw implantation. Please refer to FIG. 1C. After the creation of the screw channel, the two guiding units 94 are first screwed into the openings 922a of the top of the removable parts 922, and then a front end of the screwdriver 6 screws into the accommodating space 95 of the receiver 92 by combining the thread on the inside of the receiver 92 with the thread on the outside of the screwdriver 6. Also, the front end of the screwdriver 6 has a structure that corresponds to the groove on the upper end of the head of the screw shaft 91, such as a hexagonal structure. Therefore, after the front structure of the screwdriver 6 is passed through the inner cap 93 and screwed into the head of the screw shaft 91, the screw shaft 91 can be directly rotated by the screwdriver 6, and the preparation of the precedent device 9 before implantation is also completed. For simplicity of illustration, FIG. 1C only shows the portion of the screwdriver 6 that is engaged with the precedent device 9. Then the surgeon can use the screwdriver 6 to force the precedent device 9 to be implanted into the vertebra, and the result is shown in FIG. 1D, which shows the result of completed implantation of four precedent devices 9. It should be noted that, for simplicity of illustration, FIG. 1D only shows one guiding unit 94 on one side of the precedent device 9.

As shown in FIG. 1D, after the implantation of the precedent device 9, the guiding unit 94 will protrude from the vertebra and out of the patient's back about 3 to 8 cm, preferably 4 to 5 cm. Thus, surgeons are able to directly see the guiding unit 94 to obtain the rough implantation position and implantation trajectory of the precedent device 9 quickly, without searching for those again. In addition, the guiding unit 94 protruding from the back of the patient can be used as an indication marker to guide surgeons in moving the spinal surgical instrument along a predetermined direction (such as the direction of the guiding unit 94 in this embodiment). In other embodiments of the present invention, the guiding unit 94 might have a marker, such as a color or a mark, to facilitate surgeons to distinguish between guiding unit s on the same precedent device, or the guiding unit s on different precedent devices.

The guiding unit 94 not only indicates the location of the precedent device 9 but more importantly provides the function of guiding the spinal surgical instrument. The spinal surgical instrument of the present invention includes a guide element including a guide hole, which can pass along the guiding unit 94 on the precedent device 9. Therefore, the guide hole can guide the spinal surgical instrument along the guiding unit 94 to move toward the precedent device 9.

Figure 2:
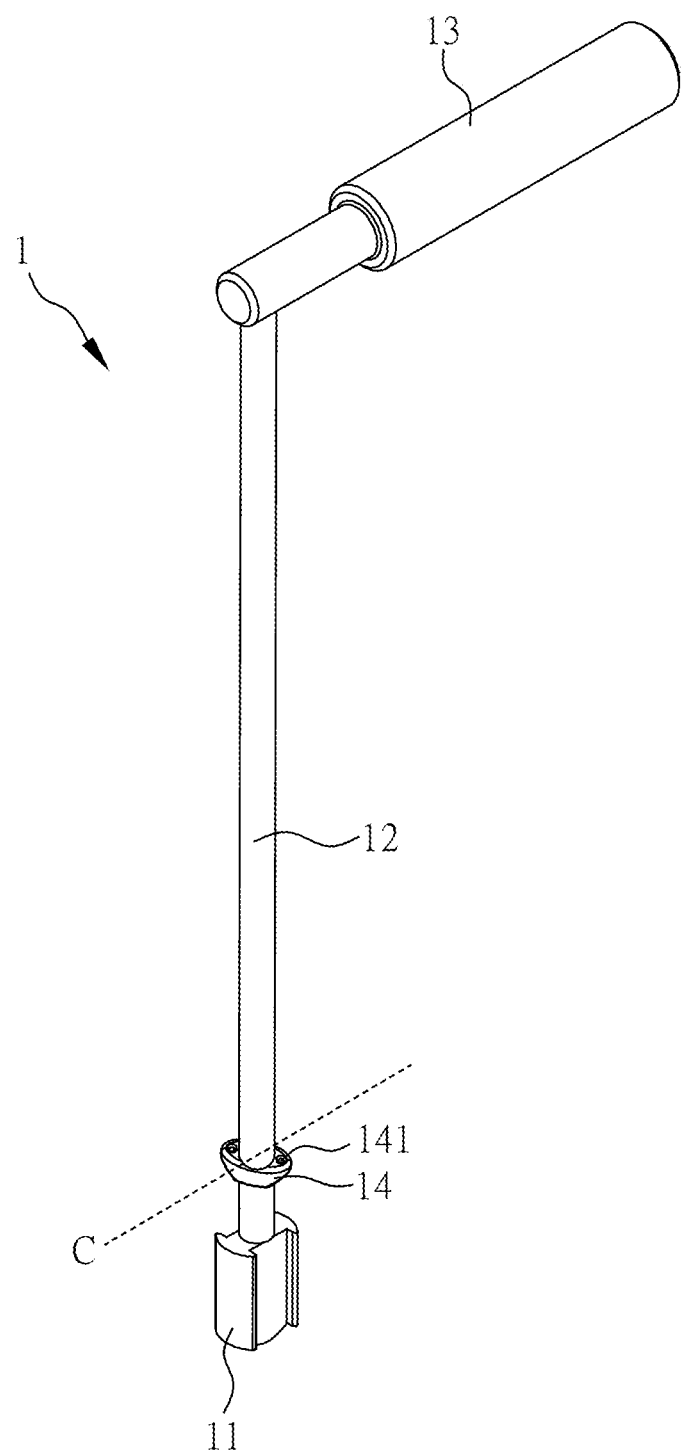
FIG. 2 is a schematic diagram of a spinal surgical instrument according to a first embodiment of the present invention.

FIG. 2 is a schematic diagram of a spinal surgical instrument according to the first embodiment of the present invention. As shown in FIG. 2, in the present embodiment, the spinal surgical instrument 1 is a pedicle screw adjuster. The spinal surgical instrument 1 includes an operating element 11, an extending element 12, a handling element 13, and a guide element 14. One end of the extending element 12 connects to the operating element 11, and the opposite end thereof connects to the handling element 13. That is, the opposite ends of the extending element 12 are the operating element 11 and the handling element 13, respectively. The operating element 11 has different configurations corresponding to functional requirements to provide the variety of functions actually required during spinal surgery. The pedicle screw adjuster in the present embodiment is used as an example; the configuration of the operating element 11 fits the accommodating space 95 of the receiver 92 and can be engaged in the receiver 92, such that the surgeon can rotate the handling element 13 clockwise or counterclockwise with the extending element 12 as the axis; meanwhile, the receiver 92 can be rotated to adjust the orientation of the U-shaped recess. Consequently, the rod 8 can be smoothly snapped into the accommodating space 95.

The extending element 12 is a long rod used for maintaining the distance between the operating element 11 and handling element 13 to keep that the applying location (the handling element 13) outside of the patient's body to facilitate the operation. In addition, the extending element 12 can increase the length of the force arm for ease of use. For more efficient and effective operation, the operating element 11 and the extending element 12 can preferably be formed integrally, but they can also be connected by other means such as a tight wedging or screw connection.

The handling element 13 provides the holding position for surgeons to control the operating element 11 by holding and manipulating the handling element 13. Similarly, the configuration of the handling element 13 can be varied to fit different types of the spinal surgical instrument 1. In the present embodiment, the handling element 13 and the extending element 12 are perpendicular to each other, or nearly perpendicular, such that the surgeon can rotate the handling element 13 with the extending element 12 as the axis.

The guide element 14 is disposed on the extending element 12 and near the operating element 11. The guide element 14 has at least one guide hole 141, and preferably two guide holes 141. Each of the guide holes 141 has two openings, which are arranged in a direction perpendicular to the extending element 12 as a center line C and disposed oppositely. During the surgery, the surgeon can refer to the guiding unit 94 protruding from patients' back, as shown in FIG. 1D, align the spinal surgical instrument 1 at the appropriate orientation, and then make the guide hole 141 pass along the guiding unit 94 such that the guide hole 141 can be moved downward along the guiding unit 94. Since the guide element 14 is fixed to the extending element 12, this action can make the entire spinal surgical instrument 1 to move in a predetermined direction (along the guiding unit 94), such that the operating element 11 can be guided to the precedent device 9 to achieve the purpose of guided positioning (referring to FIG. 5F and FIG. 5G first). Furthermore, when the guide element 14 is located at the operating element 11, the distance between the two might vary according to the function of the spinal surgical instrument 1. Thus, the guide element 14 does not actually enter the receiver 92 or connect to the receiver 92. Accordingly, the design complexity of the precedent device 9 and/or the guide element 14 is not increased. After the adjustment, the surgeon can also withdraw the spinal surgical instrument 1 along a predetermined direction by following the guiding unit 94 to avoid expanding the incision or damaging the surrounding tissue.

Figure 3:
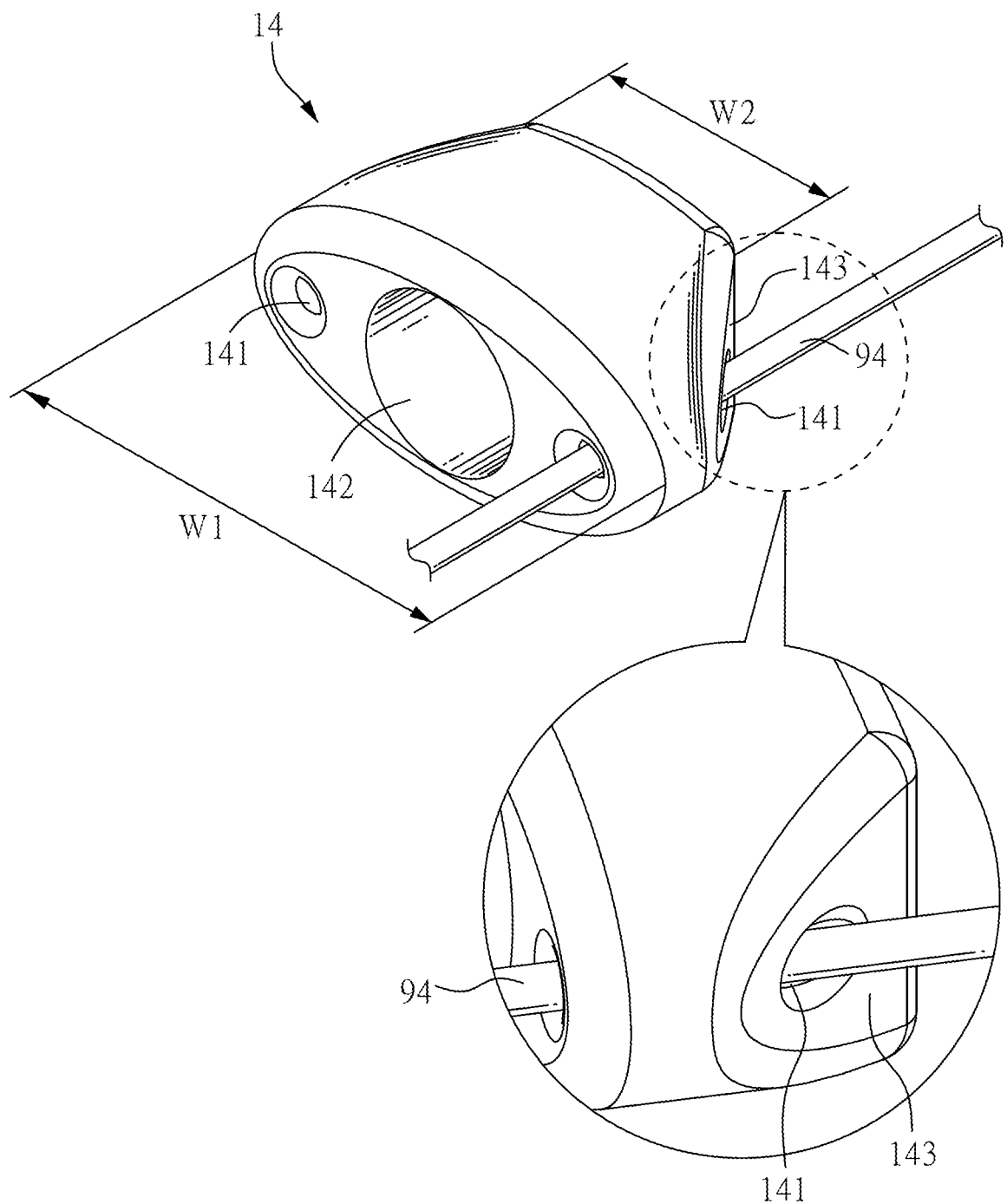
FIG. 3 is an enlarged view of the guide element shown in FIG. 2.

FIG. 3 is an enlarged view of the guide element as shown in FIG. 2, and the guiding unit 94 passes through one of the guide holes 141; please refer to FIG. 3. The guide element 14 includes a fixed hole 142, and the extending element 12 passes through the fixed hole 142, such that the guide element 14 is set and fixed to the extending element 12. Preferably, the distance between the guide element 14 and the operating element 11 is approximately shorter than 4 cm, which is shorter than the distance between the guide element 14 and the handling element 13. In other words, the guide element 14 is closer to the operating element 11 than to the handling element 13. A difference in diameter between the guiding unit 94 and the guide hole 141 would result in the guiding unit 94 shaking within the guide hole 141, such that the extending element 12 and the guiding unit 94 in the direction of the long axis would form an angle (an error). This error can be reduced by making the guide element 14 close to the operating element 11. In addition, the distance between the guide element 14 and the operating element 11 preferably strikes a balance between maintaining alignment and avoiding interference with other devices. Specifically, when the distance between the guide element 14 and the operating element 11 is shorter, it is easier for the operator to align. However, when the distance between the two is too close, the close proximity will easily interfere with other devices, such as an anti-torque wrench.

The number and locations of the guide holes 141 are preferably in conjunction with the guiding unit 94. As shown in FIG. 1A and FIG. 3, the precedent device 9 has two guiding units 94 disposed oppositely, and the guide element 14 has two guide holes 141 corresponding to the two guiding units 94. The two guide holes 141 are located at the opposite ends of a fixed hole 142 with the center line of the fixed hole 142 as the center line. Please also refer to FIG. 2. In other words, when the guide element 14 is set in the extending element 12, the two guide holes 141 are located at the opposite ends of the fixed hole 142 with the extending element 12 describing the center line.

As shown in FIG. 2 and FIG. 3, preferably, the width of the guide element 14 near the handling element 13 is greater than the width W2 near an end of the operating element 11 such that a trapezoidal-like structure are formed with two inclined planes 143 on its both sides. One end of the guide hole 141 is opened at the inclined plane 143. Since the inclined plane 143 is located near one side of the operating element 11, then when the guide hole 141 passes along the guiding unit 94, the inclined plane 143 will by design guide the guiding unit 94 into the guide hole 141 to a certain extent. Meanwhile, the inclined plane 143 will by design increase the cross-sectional area of the guide hole 141 slightly and increase the fault tolerance between the two in terms of alignment, such that the guiding unit 94 can easily pass through the guide hole 141.

Figure 4:
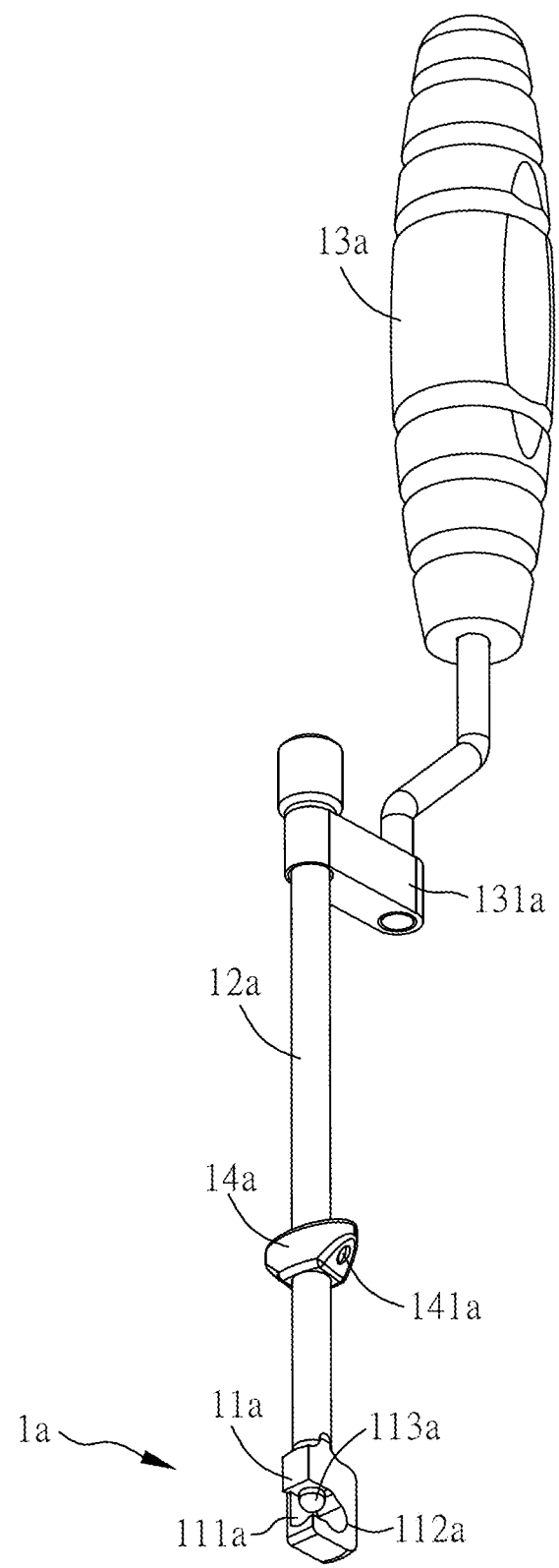
FIG. 4 is a schematic diagram of a spinal surgical instrument according to a second embodiment of the present invention.

FIG. 4 is a schematic diagram of a spinal surgical instrument according to a second embodiment of the present invention. Please refer to FIGS. 1A, 1D, 1E, and FIG. 4. The spinal surgical instrument 1*a* in the present embodiment is a rod holder, which is used to place the rod 8 at the receiver 92 or to adjust the position of the rod 8. Similarly, the spinal surgical instrument 1*a* in the present embodiment includes an operating element 11*a*, an extending element 12*a*, a handling element 13*a*, and a guide element 14*a*. The opposite ends of the extending element 12*a* connect to the operating element 11*a* and the handling element 13*a*, respectively. Just as in the first embodiment, the guide element 14*a* is set in the extending element 12*a*, and the distance between the guide element 14*a* and the operating element 11*a* is shorter than the distance between the guide element 14*a* and the handling element 13*a*. As for the remaining details, reference may be made to the aforementioned embodiment, and such details will not be further described herein. Specifically, the operating element 11*a* and the handling element 13*a* differ from those in the first embodiment in terms of the function of the rod holder.

The operating element 11*a* includes a concave portion 111*a* used for holding the rod 8. In the present embodiment, one end of the concave portion 111*a* is a closed end 112*a*, and the operating element 11*a* holds the end of the rod 8 with the open end of the concave portion 111*a*. In other embodiments, the closed end 112*a* can be removed to enable the concave portion 111*a* to laterally pass through the operating element 11*a*, such that the operating element 11*a* can hold any section of the rod 8 by means of the concave portion 111*a*, especially the intermediate section of the rod 8, to enhance the stability of the holding. Preferably, a protrusion 113*a* is disposed in the concave portion 111*a*, and the protrusion 113*a* can abut against the rod 8 disposed in the concave portion 111*a* such that the operating element 11*a* can hold the rod 8 tightly.

Also, the handling element 13*a* in the present embodiment has a rotary shaft 131*a* which enables a surgeon to adjust the position of the rod 8. By manipulating the handling element 13*a*, a surgeon can align the guide holes 141*a* with the guiding units 94 and make the guide holes 141*a* pass along the guiding units 94. By moving the guide element 14*a* along the guiding units 94, the operating element 11*a* can be guided to the receiver 92 smoothly to place the rod 8 in the receivers 92 of two adjacent precedent devices 94 so as to connect the precedent devices 94 together. It causes the rod 8 to be call a spinal fixation element as well. This design addresses the problems such as a limited operative space and narrow operative field encountered by surgeons during surgery. In traditional surgical approaches, surgeons need to separate or distract tissues from the vertebrae constantly to address those problems. Furthermore, the pair of guiding units 94, which are relatively positioned on the left and right, can represent the relative positions of the removable portions 922. Therefore, the guiding units 94 can be used to infer the orientation of the opening of the U-shaped recess, indicating the orientation to which the rod 8 should be adjusted, which can allow the surgeon to complete the steps efficiently.

Figure 5A:
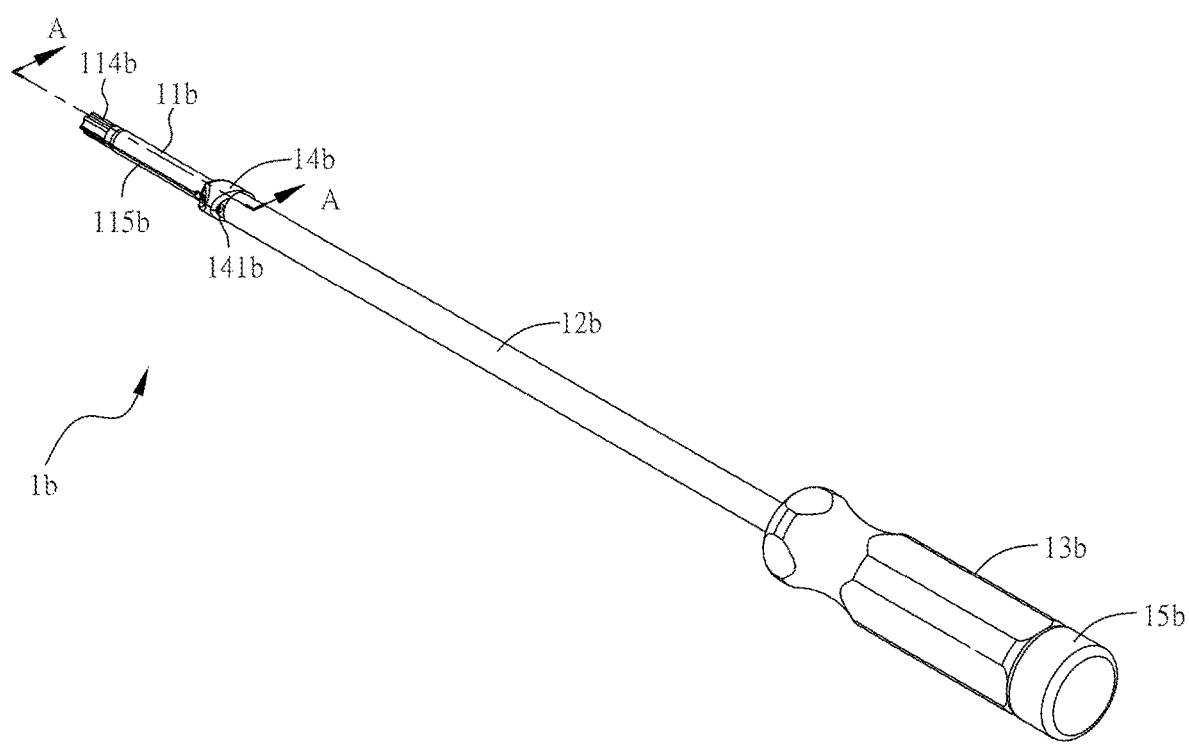
FIG. 5A is a schematic diagram of a spinal surgical instrument according to a third embodiment of the present invention.

FIG. 5A is a schematic diagram of a spinal surgical instrument according to a third embodiment of the present invention. Please refer to FIGS. 1A, 1D, 1E, and FIG. 5A. After the rod 8 is placed in the accommodating space 95 of the receiver 92, the rod 8 needs to be locked with a locking screw 7 at the bottom of the accommodating space 95 to achieve the effect of fusing adjacent vertebrae. The spinal surgical instrument used by the surgeon to lock the rod 8 includes but is not limited to a pre-lock wrench and/or an anti-torque wrench. The spinal surgical instrument 1b in the third embodiment is a pre-lock wrench. Similarly, the spinal surgical instrument 1b in the present embodiment includes an operating element 11b, an extending element 12b, a handling element 13b, and a guide element 14b. The opposite ends of the extending element 12b connect the operating element 11b and the handling element 13b, respectively. Just as in the previous embodiment, the guide element 14b is set in the extending element 12b, and the distance between the guide element 14b and the operating element 11b is shorter than that of the handling element 13b. The remaining details can be found in the aforementioned embodiments and will not be described hereafter. Specifically, in view of the function of a pre-lock wrench, the structure of the operating element 11b, extending element 12b, and handling element 13b differs from the preceding embodiment.

Figure 5B:
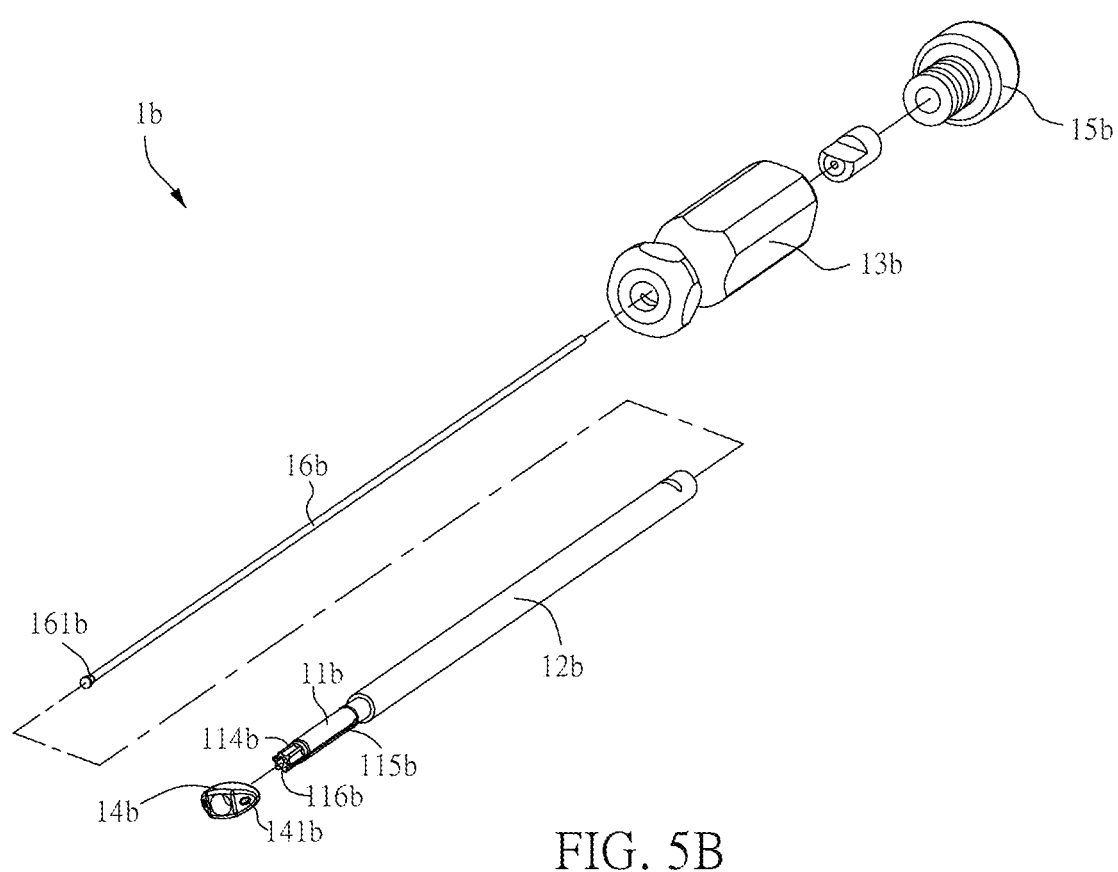
FIG. 5B is an exploded view of the spinal surgical instrument shown in FIG. 5A.
Figure 5C:
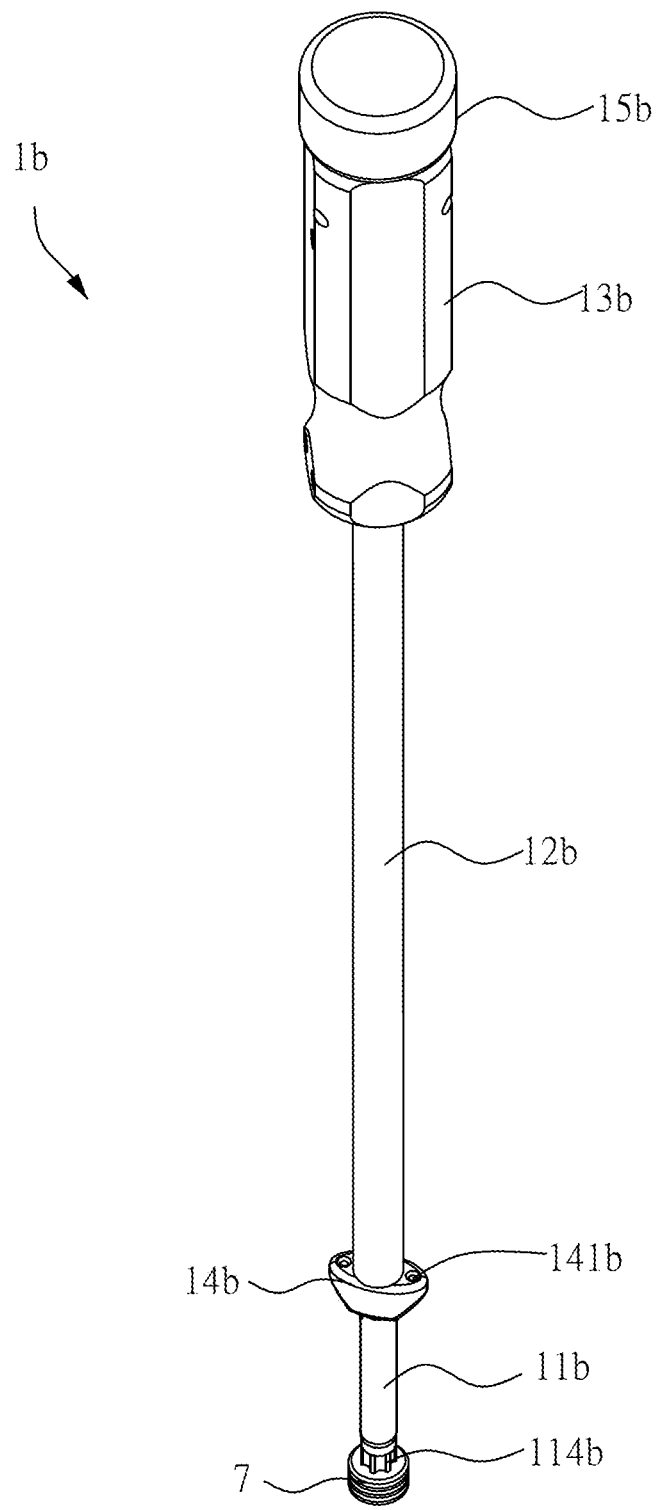
FIG. 5C is a schematic diagram showing the operating element shown in FIG. 5A connected to a locking screw.

FIG. 5B is an exploded view of the spinal surgical instrument shown in FIG. 5A, and FIG. 5C shows the operating element shown in FIG. 5A connected to a locking screw. Please refer to both FIG. 5B and FIG. 5C. Specifically, the front end of the operating element 11b in the present embodiment has an engaging structure 114b, which is matched with the top or inner ring groove of the locking screw 7. Surgeons snap the engaging structure 114b into the ring groove of the locking screw 7, such that the spinal surgical instrument 1b and the locking screw 7 are engaged securely, to achieve the purpose of holding the locking screw 7. The operating element 11b has at least one longitudinal groove 115b and an accommodating space 116b. The longitudinal groove 115b is longitudinally disposed on the side wall of the operating element 11b and communicates with the internal accommodating space 116b and the outer space. The spinal surgical instrument 1b further includes an adjustable element 15b and a rod element 16b. The adjustable element 15b is adjacent to the handling element 13b and located at one end of the handling element 13b opposite to the extending element 12b. The handling element 13b and the extending element 12b both have a pipeline therethrough. During assembly of the handling element 13b, the extending element 12b, and the operating element 11b, the accommodating space 116b can communicate to an end of the handling element 13b, The rod element 16b is disposed through the handling element 13b, the extending element 12b and part of the operating element 11b, and is accommodated in the connected channel and the accommodating space 116b. The opposite end of the rod element 16b is connected and fixed to the adjustable element 15b. When the adjustable element 15b is rotated, the rod element 16b can be driven to move within the operating element 11b to expand the operating element 11b.

Figure 5D:
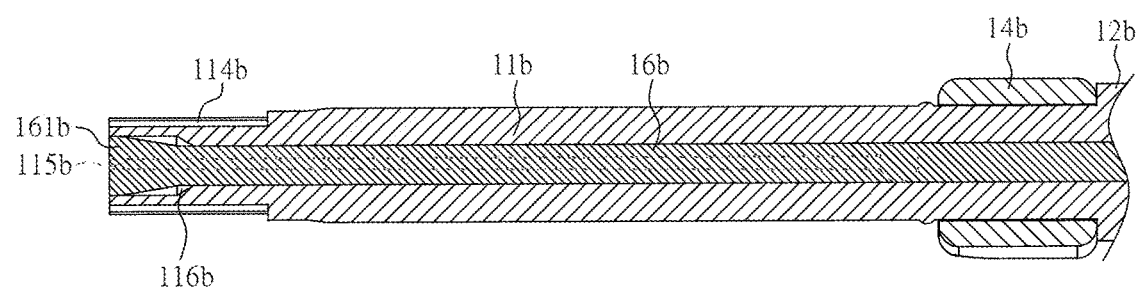
FIG. 5D is a cross-sectional view from line A-A of FIG. 5A.
Figure 5E:
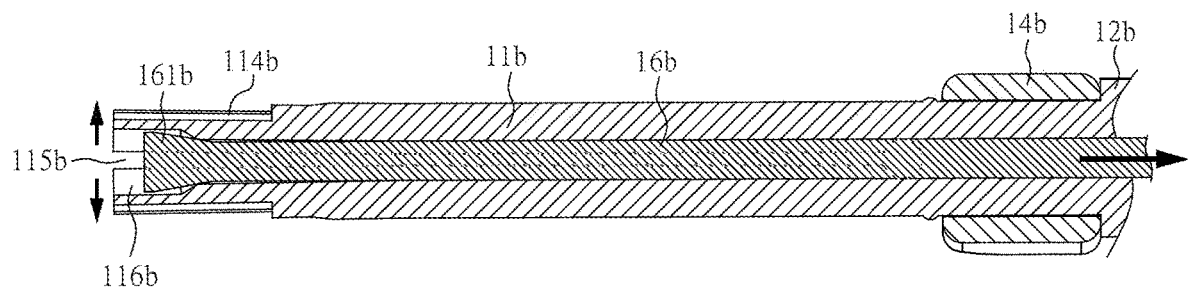
FIG. 5E is a schematic diagram showing the operation of the operating element shown in FIG. 5D being expanded.

The surgeon snaps the engaging structure 114b into a top groove of the locking screw 7, as shown in FIG. 5C, and then rotates the adjustable element 15b. When an internal thread is disposed in the channel within the handling element 13b or the extending element 12b, or disposed in the accommodating space 116b within the operating element 11b, and correspondingly an external thread is disposed on the rod element 16b, the surgeon can rotate the adjustment element 15b and drive the rod element 16b to rotate and move to one end of the handling element 13b. Please refer to FIG. 5D and FIG. 5E. Specifically, FIG. 5D is a cross-sectional view from line A-A of FIG. 5A, and FIG. 5E is a schematic diagram showing the operation of the operating element in FIG. 5D being expanded. The rod element 16b includes an expansion head 161b, which is accommodated in the accommodating space 116b, and the slope of the outer wall of the expansion head 161b is greater than the slope of the inner wall of the rear end of the accommodating space 116b. When the rod element 16b moves toward the handling element 13b, the expansion head 161b also retracts in the same direction; therefore, the expansion head 161b applies an outward expanding force to the inner wall of the accommodating space 116b, as shown in FIG. 5E. Since a longitudinal groove 115b is opened on the side wall of the operating element 11b, the side wall of the operating element 11b has the flexibility to expand outward, making the outward expansion of the operating element 11b greater. Thus, the engaging structure 114b and the locking screw 7 can be more closely connected such that the engagement of the spinal surgical instrument 1b and the locking screw 7 can be more secure and thereby reduce the chance that the locking screw 7 might be dislodged by a collision with the surrounding tissue.

Figure 5F:
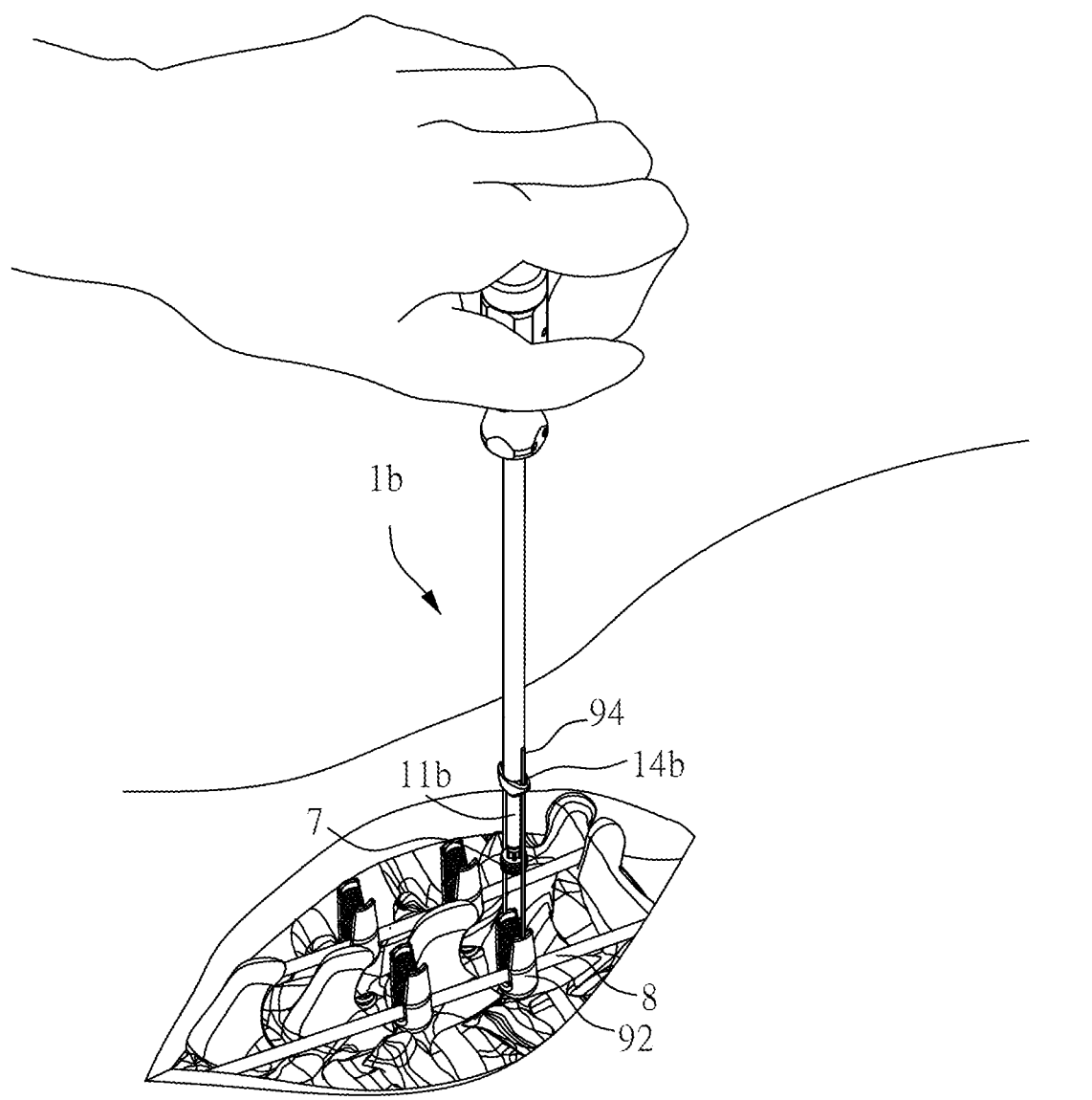
FIG. 5F and FIG. 5G show the operation of the spinal surgical instrument shown in FIG. 5A.
Figure 5G:
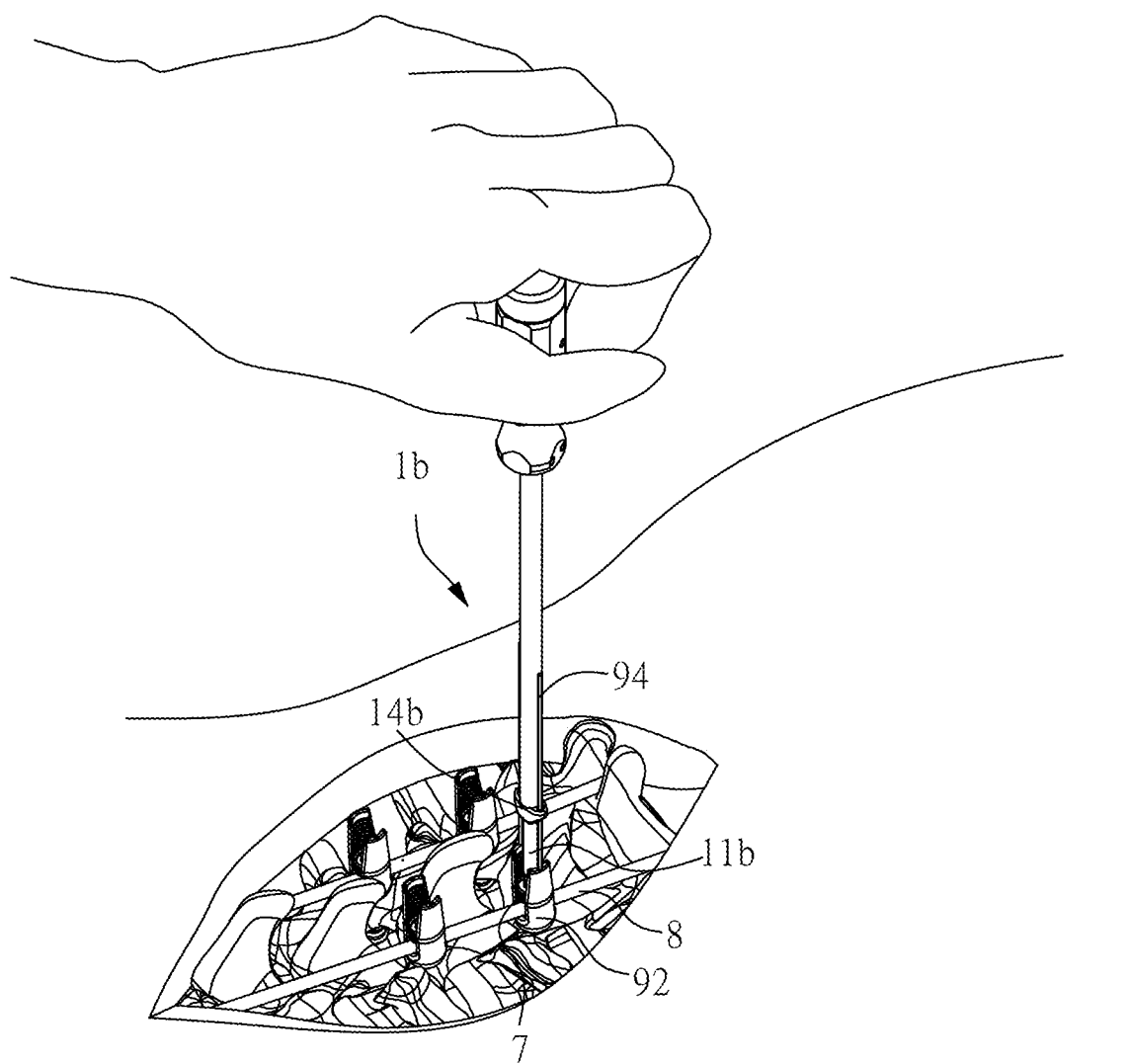

FIG. 5F and FIG. 5G are schematic diagrams showing the operation of the spinal surgical instrument shown in FIG. 5A. Please refer to both FIG. 5F and FIG. 5G. As described above, the surgeon will move the spinal surgical instrument 1b, which is securely engaged with the locking screw 7, toward the guiding unit 94 and then align the guiding units 94 and pass them through the guide holes 141b such that the operating element 11b can be guided to the receiver 92, whereupon the locking screw 7 can be smoothly locked down into the receiver 92 and the rod 8 can be pressed to be positioned. When the rod 8 is fixed, the surgeon can rotate the adjustable element 15b in reverse such that the expansion head 161b moves forward to the operating element 11b, the side wall of the operating element 11b is restored to its original state, and the locking screw 7 is released from the spinal surgical instrument 1b. In other embodiments of the present invention, through the opposite configuration design, when the expansion head 161b moves toward to the operating element 11b, the side wall of the operating element 11b will expand outward. Also, the side wall is restored to its original state after moving toward to the handling element 13b.

Figure 6A:
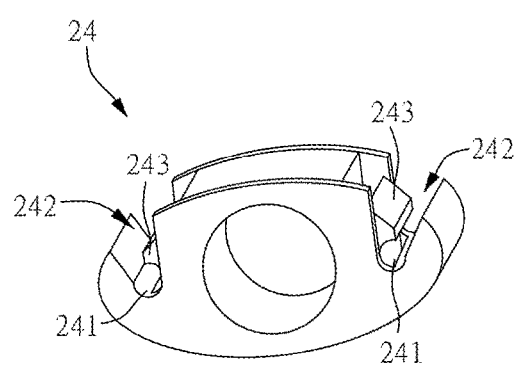
FIG. 6A and FIG. 6B are schematic diagrams showing another variation of the guide element shown in FIG. 3.
Figure 6B:
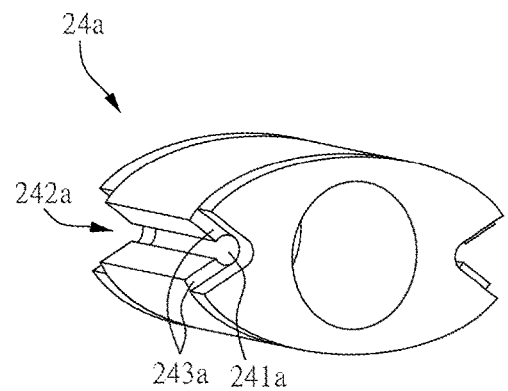

It should be noted that the guide elements 14, 14a, 14b in the aforementioned embodiment are similar trapezoidal structures, as shown in the figure illustrating the first embodiment, and they are set in the extending element 12, but the present invention does not limit the appearance of the guide element 14, also as shown in FIG. 6A and FIG. 6B. FIG. 6A and FIG. 6B are schematic diagrams of another variation of the guide element shown in FIG. 3. Please first refer to FIG. 2 and FIG. 6A. The guide element 24 has a groove 242 which is located at the periphery of the guide hole 241, and the guide hole 241 communicates with the outer space via the groove 242. The groove 242 is provided such that the surgeon can cause the groove 242 of the guide element 24 to approach the guiding unit 94 and then insert the guiding unit 94 into the guide hole 241 via the groove 242 such that the guide hole 241 passes along the guiding unit 94.

Preferably, the guide element 24 further has a blocker 243 located between the groove 242 and the guide hole 241 and at one side of the groove 242. When surgeons move the groove 242 of the guide element 24 contact the guiding unit 94, the blocker 243 can be bent or expanded at the same time such that the guiding unit 94 can be fitted into the guide hole 241 smoothly. When the guiding unit 94 is inserted, the blocker 243 returns to its original state to restrict the guiding unit 94 in the guide hole 241 from becoming easily detached from the guide hole 241. In practice, the blocker 243 preferably has a property of bendability or springback, such as that of a thin metal ribbon or metal sheet.

In other embodiments, as shown in FIG. 6B, the blocker 243a of the guide element 24a may also be a soft material. Furthermore, the blocker 243a made of soft material may be located on both sides of the groove 242a. When the guiding unit 94 contacts the blocker 243a, the blocker 243a is compressed such that the guiding unit 94 can fit into and pass through the guide hole 241a. After the guiding unit 94 is fitted into the guide hole 241a, the blocker 243a returns to its original state.

Figure 7:
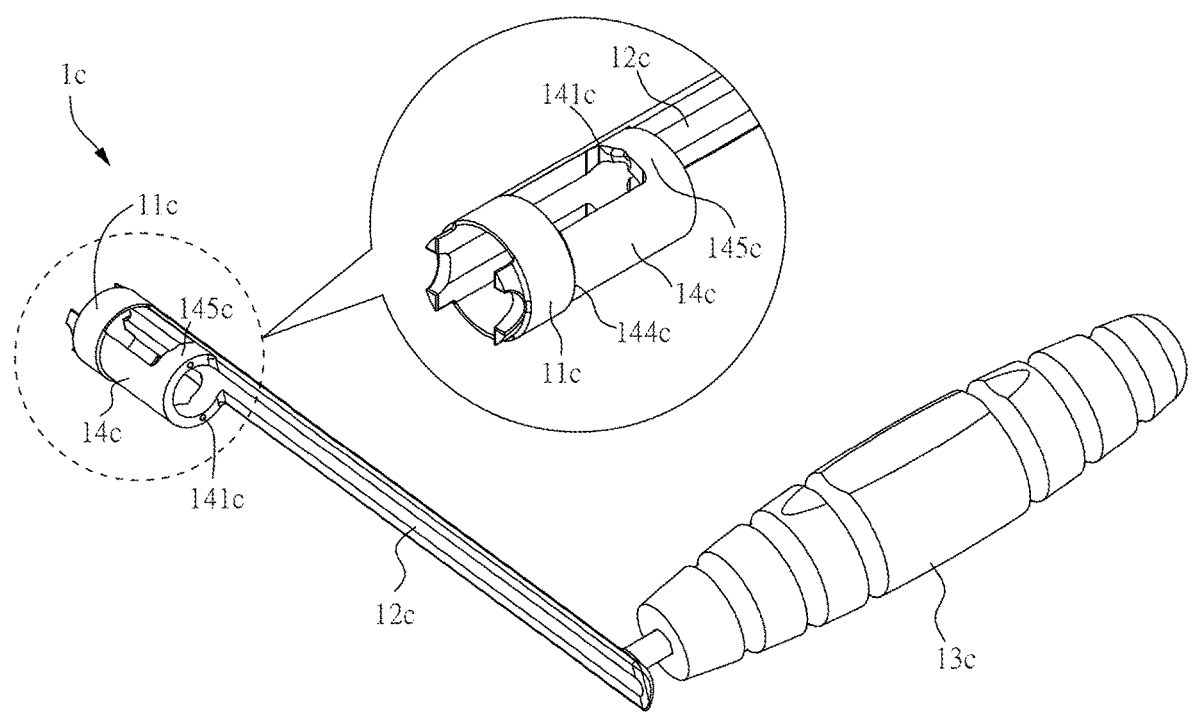
FIG. 7 is a schematic diagram of a spinal surgical instrument according to a fourth embodiment of the present invention.

FIG. 7 is a schematic diagram of a spinal surgical instrument according to a fourth embodiment of the present invention. Please refer to all of FIGS. 1A, 1D, 1E and FIG. 7. The spinal surgical instrument 1c in the present embodiment is an anti-torque wrench, which includes an operating element 11c, an extending element 12c, a handling element 13c, and a guide element 14c. The two ends of the extending element 12c connect with the operating element 11c and the handling element 13c, respectively. The guide element 14c is disposed at the extending element 12c. In view of the function of the anti-torque wrench, the structure of the operating element 11c, extending element 12c, and guide element differs slightly from the preceding embodiment.

The bottom of the operating element 11c has a plurality of pins for securing the corresponding locking ends, such as the outside of the receiver 92, to counter the torque generated by the use of the pre-lock wrench to lock the locking screw 7 in the receiver 92 and prevent the rotation of the receiver 92 while the locking screw 7 is being locked. Accordingly, the locking screw 7 can be locked securely such that screw loosening can be avoided. The operating element 11c is a columnar hollow structure that can be used to hold the receiver 92. The upper opening of the operating element 11c allows the operating element 11b of the other spinal surgical instrument 1b (pre-lock wrench) to enter and operate to, for example, lock the locking screw 7 to secure the rod 8.

In the present embodiment, the extending element 12c connects to a part of the side wall on the operating element 11c. The distance between the guide element 14c and the operating element 11c is about 0 mm. In other words, the guide element 14c can directly connect to the operating element 11c and the extending element 12c. Specifically, the structure of the guide element 14c corresponds to the operating element 11c; said structure is similar to an annular hollow structure. Also, the guide element 14c has a bottom edge 144c and a side wall 145c. The bottom edge 144c connects to an operating element 11c, and the side wall 145c partially connects to the extending element 12c. Preferably, the operating element 11c, the extending element 12c, and the guide element 14c are a one-piece structure, and the guide hole 141c runs through the side wall 145c such that the guide hole 141c can pass along the guiding unit 94.

The surgeon can make the guiding hole 141c of the guide element 14c pass along the guiding unit 94 such that the operating element 11c approaches and settles on the outside of the receiver 92. Then the surgeon uses the spinal surgical instrument 1b (the pre-lock wrench) in the third embodiment in conjunction with the locking screw 7. The operating element 11b and the locking screw 7 are guided into the receiver 92 together for screwing the locking screw 7 within the receiver 92. In one aspect, the surgeon can use one hand to clasp the spinal surgical instrument 1b (the pre-lock wrench) to fix the rod 8 by locking the locking screw 7 and, meanwhile, uses the other hand to manipulate the spinal surgical instrument 1c (the anti-torque wrench) to stabilize the receiver 92 for preventing rotation caused by the action of screwing locking screw 7.

Figure 8:
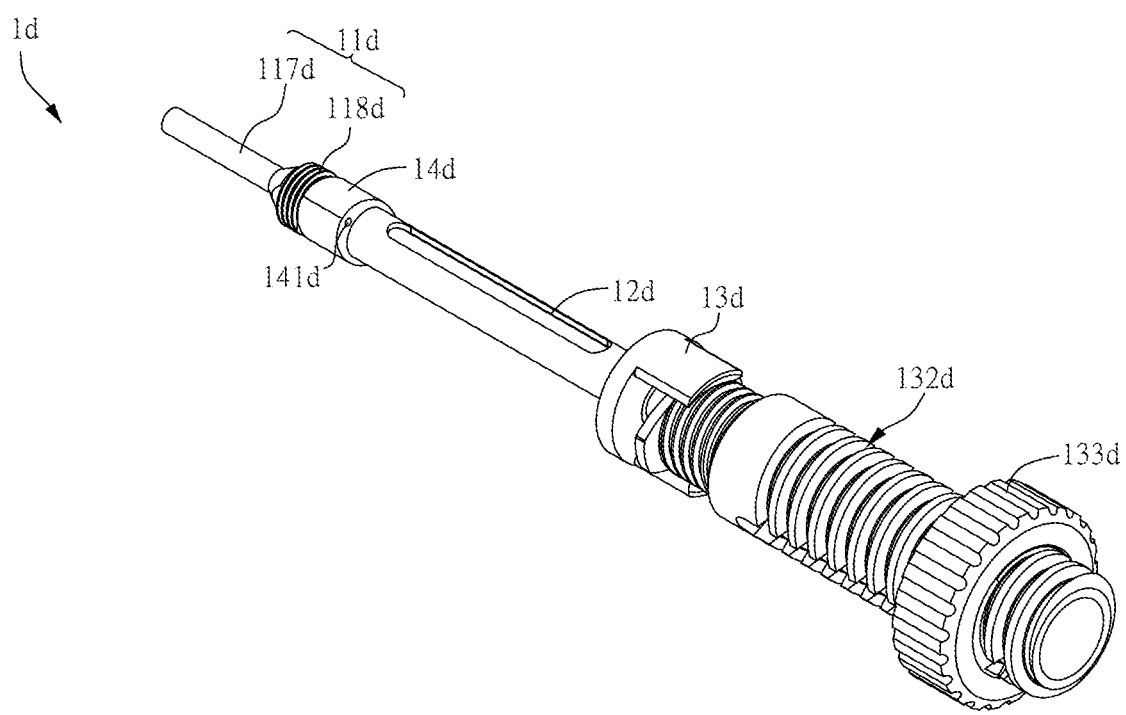
FIG. 8 is a schematic diagram of a spinal surgical instrument according to a fifth embodiment of the present invention.

FIG. 8 is a schematic diagram of a spinal surgical instrument according to a fifth embodiment of the present invention. Please refer to FIGS. 1A, 1D, 1E, and FIG. 8. The spinal surgical instrument 1d in the fifth embodiment is a bone cement or repair material injector which can be applied in spinal surgery applying bone cement, bone graft or other repair material. It should be noted that the screw shaft 91 used in conjunction with the spinal surgical instrument 1d in the present embodiment is a screw shaft 91 having an injection channel (not shown). After implantation of the precedent device 9, the bone cement or other repair material can be injected into the vertebrae by using the spinal surgical instrument 1d.

The spinal surgical instrument 1d includes an operating element 11d, an extending element 12d, a handling element 13d, and a guide element 14d. The two ends of the extending element 12d connect with the operating element 11d and the handling element 13d, respectively. The guide element 14d is disposed on the extending element 12d. Specifically, in the present embodiment, the guide element 14d is set in the extending element 12d, and the guide element 114d is directly set in an end of the extending element 12d; the end is connected to the operating element 11d such that the distance between the guide element 14d and the operating element 11d is about 0 mm. In view of the function of the bone cement or repair material injector, the operating element 11d in the present embodiment includes an injection head 117d. The interior of the extending element 12d can accommodate bone graft, bone cement or other repair material, or a syringe with bone graft, bone cement or other repair material. The spinal surgical instrument 1d is equipped with a pushing element in the rear of the handling element 13d for extruding bone graft, bone cement, or other repair material. In the present embodiment, the pushing element is a rotatable pushing column 132d. The rotatable pushing column 132d includes a pushing knob 133d and an inner pushing column. The pushing knob 133d has an upper limit ring and a lower limit ring, which define a limited space together. The outer circumference of the inner pushing column has a locating ring, which extends outward from the outer circumference of the inner pushing column and is accommodated in the limited space. Therefore, when the pushing knob 133d is rotated, the inner pushing column will be driven to move forward without rotation. The abovementioned structure and mechanism can address the problem of the rupture or fracture of the plunger of the syringe during injection of bone graft, bone cement or other repair material. In detail, the mobility and rotatability of the plunger in the syringe will diminish over time in order of the gradual hardening of the injection material. If the plunger is driven to move forward by the rotating inner pushing column, it will generate torque on the plunger. Once the increasing torque exceeds the bearing limitation of the plastic material of the plunger, it results in the rupture or fracture of the plunger and interruption of the injection process.

As mentioned in the previous embodiments, the surgeon can make the guide hole 141d pass along the guiding unit 94 to guide the operating element 11d to the receiver 92. Afterwards, the external thread 118d on the operating element 11d can operate with the thread on the inside of the receiver 92 such that the two are stably engaged, and the injection head 117d can be inserted into the injection channel of the screw shaft 91. Next, the surgeon can rotate the pushing knob 133d to push the inner pushing column and then push the plunger of the injection syringe, and the bone graft, bone cement or other repair material will be injected into the vertebra or other bone tissue.

Figure 9A:
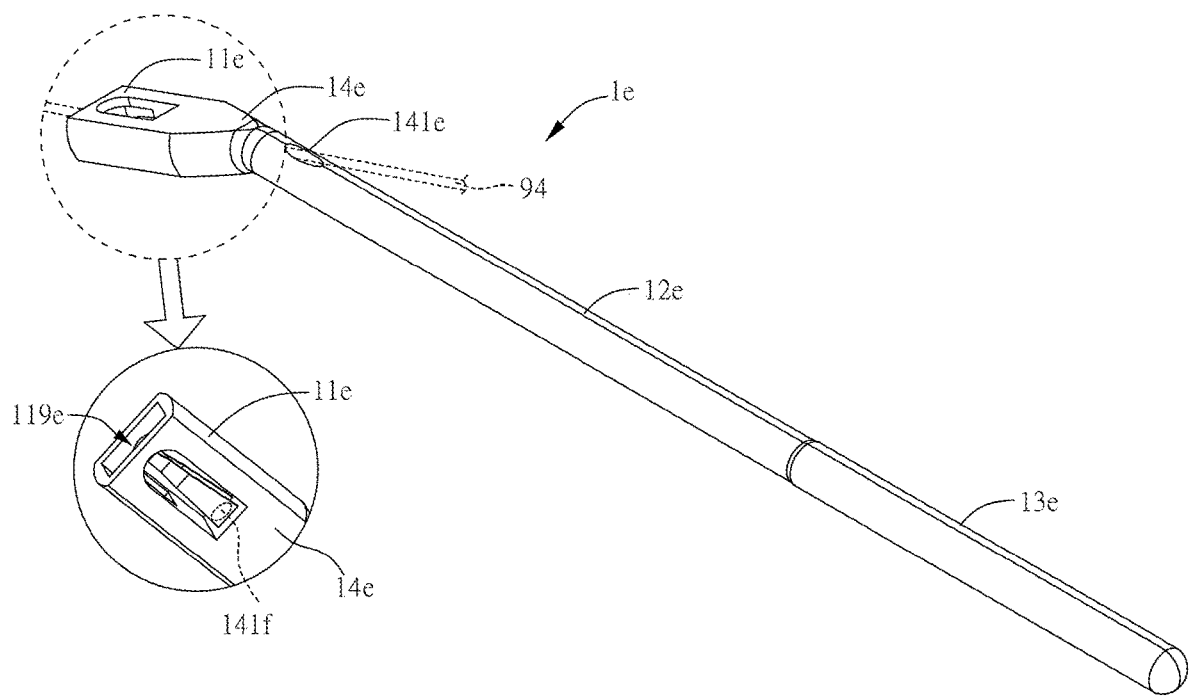
FIG. 9A is a schematic diagram of a spinal surgical instrument according to a sixth embodiment of the present invention.

FIG. 9A shows a spinal surgical instrument according to a sixth embodiment of the present invention. Please refer to FIGS. 1A, 1D, 1E, and FIG. 9A. A receiver 92 has a removable part 922. The aforementioned guiding unit 94 is set at the upper surface of the removable part 922. After the rod 8 is fixed, the surgeon has to use a breaker to remove the removable part 922. The spinal surgical instrument 1e in the present embodiment is a breaker. Similarly, the spinal surgical instrument 1e in the present embodiment includes an operating element 11e, an extending element 12e, a handling element 13e, and a guide element 14e. The two ends of the extending element 12e connect with the operating element 11e and the handling element 13e, respectively.

Figure 9B:
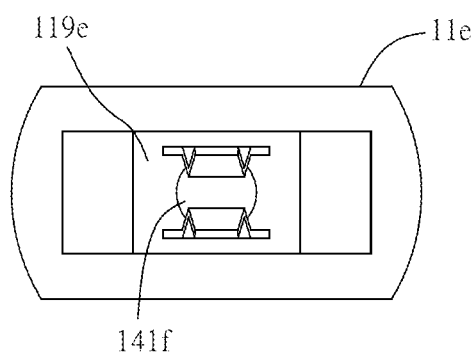
FIG. 9B is an internal schematic diagram of the operating element shown in FIG. 9A.

FIG. 9B is an internal schematic diagram of the operating element shown in FIG. 9A. As shown in FIG. 9B, the operating element 11e in the present embodiment includes an accommodating space 119e, which has a shape corresponding to removable part 922 such that it can fit onto the removable part 922 of the receiver 92. In the present embodiment, the guide element 14e includes two guide holes 141e, 141f that communicate with each other. Specifically, one of the guide holes 141e is adjacent to the extending element 12e, and the other guide hole 141f is adjacent to the operating element 11e and located at the upper end of the accommodating space 119e.

The surgeon can make the operating element 11e approach the guiding unit 94 on one side of the receiver 92, and then make the guiding unit 94 pass from the guide hole 141f at the top of the accommodating space 119e to the her guide hole 141e, as shown by the arrow symbol in FIG. 9A. This motion guides the accommodating space 119e of the operating element 11e to settle onto the removable part 922 smoothly. That is, the removable part 922 can be precisely inserted into the accommodating space 119e. Then the surgeon can force the handling element 13e outward pull off the removable part 922. After the removable part 922 is snapped off, the spinal surgical instrument 1e and the broken removable part 922 can be removed the same guide direction.

It should be noted that the structure, size, material and other specific content in any embodiment of the present invention is not particularly limited to the described embodiment, except that the different parts of the spinal surgical instrument in terms of technical essence due to function differences can be extended to other embodiments as a reference, especially the guide element.

In addition, the present invention further provides a method of guiding a spinal surgical instrument to a precedent device. For the precedent device, refer to the precedent device 9 in the aforementioned embodiment, which includes at least a guiding unit. The spinal surgical instrument includes an operating element, an extending element, a handling element, and a guide element. One end of the extending element connects to the operating element, and the opposite end thereof connects to the handling element. The guide element disposed at the extending element includes at least a guide hole. As for the structural features of the respective elements and their connection relationships, reference may be made to any of the spinal surgical instruments 1, 1a, 1b, 1c, 1d, 1e in the aforementioned embodiments, so such details will not be further described herein.

Figure 10:
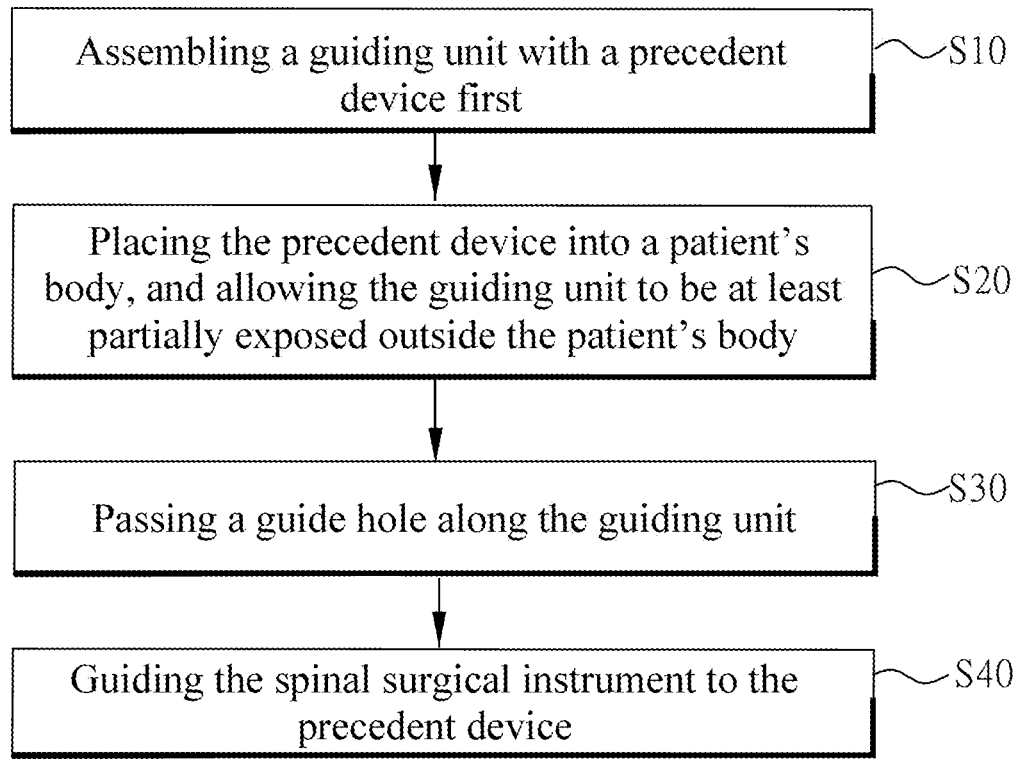
FIG. 10 is a flowchart showing a method of guiding a spinal surgical instrument to a precedent device according to an embodiment of the present invention.

FIG. 10 is a flowchart showing a method of guiding a spinal surgical instrument to a precedent device according to an embodiment of the present invention. Please refer to FIG. 10. The method according to the present embodiment is a method for a surgeon to operate a spinal surgical instrument, which includes the steps of: assembling a guiding unit with a precedent device first (Step S10); placing the precedent device into a patient's body, and allowing the guiding unit to be at least partially exposed outside the patient's body (Step S20); passing a guide hole along the guiding unit (Step S30); and guiding the spinal surgical instrument to the precedent device (Step S40). Specifically, Step S10 relates to the assembly of the precedent device and its guiding unit (refer to the aforementioned description of FIG. 1Aa and FIG. 1B for details). Step S20 relates to the method and instrument for placing the precedent device in the patient's body (refer to the aforementioned description of FIG. 1C and that of FIG. 1D regarding the guiding unit being at least partially exposed outside the patient's body). For Step S30 and Step S40, passing the guide hole over the guiding unit and guiding the spinal surgical instrument to the precedent device, refer to the actuation relationship between the spinal surgical instrument and the precedent device in the first embodiment to the sixth embodiment described above. In the example of FIGS. 5C, 5F, and 5G, after the guide hole 141b is passed along the guiding unit 94, the spinal surgical instrument 1b can be further guided to the precedent device 9. Specifically, the guide hole 141b can be moved along the guiding unit 94 toward the receiver 92 of the precedent device 9 such that the operating element 11b can further approach the receiver 92. The operating elements of other types of surgical instruments, such as a pedicle screw adjuster, a bone cement or repair material injector, an anti-torque wrench or a breaker, can also be engaged with a component of a precedent device.

As described above, a spinal surgical instrument and a method of guiding thereof according to the present invention are operated with the precedent device having the guiding unit. The spinal surgical instrument includes an operating element, an extending element, a handling element, and a guide element. Two ends of the extending element are connected with the operating element and the handling element, respectively. In addition, the guide element is disposed on the extending element, and the guide element has a guide hole. By aligning the guide hole with the guiding unit and then passing the guiding unit through the guide hole, the surgeon can move the spinal surgical instrument along the guiding unit in a predetermined direction to drive the spine moving instrument to move in a desired direction such that the operating element will effectively and efficiently approach the precedent device for subsequent moves. Therefore, the design of the present invention addresses the problems off limited operative space and narrow operative field encountered by surgeons during surgery. In addition, the use of the present invention can reduce the influence of the adverse effects of retraction or detachment of tissue, improve the success rate of surgery, reduce the operation time and shorten the period of postoperative recovery.

In addition, the spinal surgical instrument of the present invention can be any instrument used for placing a pedicle screw fixation system or cortical bone trajectory (CBT) screw technique. Thus, even if surgeons have to use multiple instruments during the whole procedure, each of the instruments can be guided to move along a determined path following the guiding unit as the guiding unit passes through the guide hole. In this way, the surgeon can ensure that the spinal surgical instruments can move toward or away from the screw along the original path to reduce the expansion of an incision.

Especially for minimally invasive surgery, since the guiding unit of a precedent device can protrude from a surgical incision on the back of a patient, the surgeon can easily locate an implanted or precedent device. It is also useful for surgeons to identify or align the approach direction of surgical instruments with the guiding unit during the subsequent moves.

The objective, means, and efficiency of the present invention are all different from conventional characteristics in the prior art. It will be appreciated if the committee can review and grant a patent for the benefit of society. However, it should be noted that the described embodiments are only for illustrative and exemplary purposes, and that various changes and modifications may be made to the described embodiments without departing from the scope of the invention as disposed by the appended claims.

What is claimed is:

1. A spinal surgical instrument operated with a precedent device including at least one guiding unit, the spinal surgical instrument comprising:
    an operating element having at least one longitudinal groove;
    an extending element, one end of which is connected to the operating element;
    a handling element, which is connected to the opposite end of the extending element;
    a guide element, which is disposed on the extending element and has at least one guide hole; by passing of the at least one guide hole along the at least one guiding unit, the spinal surgical instrument is guided to the precedent device;
    an adjustable element, which is adjacent to the handling element; and
    a rod element, which is disposed through the handling element, the extending element, and part of the operating element, the rod element being movably connected with the adjustable element, and an opposite end thereof being accommodated in the operating element; the adjustable element being moved to drive the rod element to move within the operating element such that the operating element expands.

2. The spinal surgical instrument as claimed in claim 1, wherein the guide element is set in the extending element or integrally formed with the extending element.

3. The spinal surgical instrument as claimed in claim 2, wherein a distance between the guide element and the operating element is shorter than a distance between the guide element and the handling element.

4. The spinal surgical instrument as claimed in claim 3, wherein the distance between the guide element and the operating element is about 0 mm.

5. The spinal surgical instrument as claimed in claim 1, wherein a width of the guide element close to one end of the handling element is greater than a width of the guide element close to one end of the operating element.

6. The spinal surgical instrument as claimed in claim 1, wherein the guide element has a groove located at a periphery of the at least one guide hole, by which the guide hole communicates with an outer space.

7. The spinal surgical instrument as claimed in claim 6, wherein the guide element has a blocker located between the groove and the at least one guide hole.

8. The spinal surgical instrument as claimed in claim 1, wherein the at least one guide hole comprises at least two guide holes located on opposite sides of the extending element along a center line described by an extension of the extending element.

9. The spinal surgical instrument as claimed in claim 1, wherein the operating element has an accommodating space, the rod element has an expansion head accommodated in the accommodating space, and an outer wall slope of the expansion head is greater than an inner wall slope of the accommodating space.

10. The spinal surgical instrument as claimed in claim 1, wherein a distance between the guide element and the operating element is about 0 mm, and the guide element has a bottom edge and a side wall, wherein the bottom edge is connected to the operating element, and the side wall is partially connected to the extending element.

11. The spinal surgical instrument as claimed in claim 10, wherein the at least one guide hole runs through the side wall.

12. The spinal surgical instrument as claimed in claim 1, wherein the at least one guide hole comprises at least two guide holes, one of which is adjacent to the extending element and the other of which is adjacent to the operating element, and the guide holes communicate with each other.

13. The spinal surgical instrument as claimed in claim 1, wherein the spinal surgical instrument is a pre-lock wrench, a pedicle screw adjuster, a rod holder, a bone cement or repair material injector, an anti-torque wrench, or a breaker.

14. A system for bone stabilization, comprising:
    a first precedent device that includes at least one first guiding unit;
    a second precedent device that includes at least one second guiding unit;
    a spinal fixation element; and
    at least one spinal surgical instrument comprising:
        an operating element having at least one longitudinal groove;
        an extending element, one end of which is connected to the operating element; a handling element, which is connected to an opposite end of the extending element;
        a guide element, which is disposed on the extending element and has at least one guide hole; by the passing of the at least one guide hole along the at least one first and at least one second guiding units, the spinal surgical instrument is guided to the first and second precedent devices to connect them with the spinal fixation element;
        an adjustable element, which is adjacent to the handling element; and
        a rod element, which is disposed through the handling element, the extending element, and part of the operating element, the rod element being movably connected with the adjustable element, and an opposite end thereof being accommodated in the operating element; the adjustable element being moved to drive the rod element to move within the operating element such that the operating element expands.

15. The system as claimed in claim 14, wherein the spinal surgical instrument is a pre-lock wrench, a pedicle screw adjuster, a rod holder, a bone cement or repair material injector, an anti-torque wrench, or a breaker.

* * * * *